(12) United States Patent
Kovach et al.

(10) Patent No.: US 10,905,539 B2
(45) Date of Patent: Feb. 2, 2021

(54) SELF-EXPANDING, BALLOON EXPANDABLE STENT-GRAFTS

(71) Applicant: W. L. Gore & Associates, Inc., Newark, DE (US)

(72) Inventors: Larry J. Kovach, Flagstaff, AZ (US); Raymond W. Uerling, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 903 days.

(21) Appl. No.: 14/489,145

(22) Filed: Sep. 17, 2014

(65) Prior Publication Data

US 2015/0005870 A1    Jan. 1, 2015

Related U.S. Application Data

(63) Continuation-in-part of application No. 14/198,901, filed on Mar. 6, 2014, now Pat. No. 9,522,072.

(Continued)

(51) Int. Cl.
*A61F 2/07* (2013.01)
*A61L 31/14* (2006.01)
(Continued)

(52) U.S. Cl.
CPC .............. *A61F 2/07* (2013.01); *A61L 31/022* (2013.01); *A61L 31/10* (2013.01); *A61L 31/14* (2013.01); *A61F 2/89* (2013.01)

(58) Field of Classification Search
CPC ........... A61F 2/82–945; A61F 2/04–2002/077; A61F 2/958–2002/9586
See application file for complete search history.

(56) References Cited

U.S. PATENT DOCUMENTS

| 4,877,661 | A | | 10/1989 | House et al. |
| 5,192,297 | A | * | 3/1993 | Hull .......................... A61F 2/06 |
| | | | | 604/103.05 |

(Continued)

FOREIGN PATENT DOCUMENTS

| EP | 0 759 730 | 2/1999 |
| EP | 0 821 648 | 9/2001 |

(Continued)

OTHER PUBLICATIONS

International Search Report and Written Opinion for PCT/US2014/021554 dated Aug. 22, 2014, corresponding to U.S. Appl. No. 14/198,901, 7 pages.

(Continued)

*Primary Examiner* — Tan-Uyen T Ho
*Assistant Examiner* — Charles M Wei

(57) ABSTRACT

A stent-graft having a smaller compacted diameter suitable to allow the stent-graft to be transported through a body conduit to a desired site. The stent-graft is deployed at the desired site by self-expanding to a first larger diameter from the smaller compacted diameter. The stent-graft has at least one flared end when self-expanded to the first larger diameter. The stent graft is further diametrically expandable by the application of force such as the inflation of a catheter balloon within the stent-graft to a still larger, maximum second diameter that is equal to about the maximum diameter of the flared end.

30 Claims, 19 Drawing Sheets

Related U.S. Application Data

(60) Provisional application No. 61/787,989, filed on Mar. 15, 2013.

(51) Int. Cl.
*A61L 31/10* (2006.01)
*A61L 31/02* (2006.01)
*A61F 2/89* (2013.01)

(56) References Cited

U.S. PATENT DOCUMENTS

| | | | |
|---|---|---|---|
| 5,308,664 A | 5/1994 | House et al. | |
| 5,620,763 A | 4/1997 | House et al. | |
| 5,645,559 A * | 7/1997 | Hachtman | A61F 2/07 606/198 |
| 5,716,393 A * | 2/1998 | Lindenberg | A61F 2/91 623/1.2 |
| 5,735,892 A | 4/1998 | Myers et al. | |
| 5,741,333 A * | 4/1998 | Frid | A61F 2/90 623/1.18 |
| 5,755,769 A * | 5/1998 | Richard | A61F 2/90 623/1.2 |
| 5,788,626 A | 8/1998 | Thompson | |
| 5,800,512 A | 9/1998 | Lentz et al. | |
| 5,843,158 A * | 12/1998 | Lenker | A61F 2/07 623/1.13 |
| 5,843,173 A | 12/1998 | Shannon et al. | |
| 5,888,201 A * | 3/1999 | Stinson | A61F 2/90 606/191 |
| 5,899,935 A * | 5/1999 | Ding | A61F 2/90 623/1.53 |
| 5,925,074 A | 7/1999 | Gingras et al. | |
| 5,968,070 A | 10/1999 | Bley et al. | |
| 5,968,091 A * | 10/1999 | Pinchuk | A61F 2/07 427/2.24 |
| 6,036,724 A | 3/2000 | Lentz et al. | |
| 6,176,875 B1 * | 1/2001 | Lenker | A61F 2/07 623/1.49 |
| 6,217,609 B1 * | 4/2001 | Haverkost | A61F 2/90 623/1.13 |
| 6,241,757 B1 * | 6/2001 | An | D04G 1/06 623/1.1 |
| 6,245,100 B1 * | 6/2001 | Davila | A61F 2/07 606/198 |
| 6,315,708 B1 * | 11/2001 | Salmon | A61F 2/90 600/3 |
| 6,315,791 B1 | 11/2001 | Gingras et al. | |
| 6,336,937 B1 * | 1/2002 | Vonesh | A61F 2/07 623/1.13 |
| 6,350,277 B1 * | 2/2002 | Kocur | A61F 2/90 623/1.11 |
| 6,497,722 B1 | 12/2002 | Von Oepen et al. | |
| 6,613,077 B2 * | 9/2003 | Gilligan | A61F 2/86 623/1.12 |
| 6,629,992 B2 * | 10/2003 | Bigus | A61F 2/07 606/194 |
| 6,663,664 B1 * | 12/2003 | Pacetti | A61F 2/91 623/1.15 |
| 6,673,102 B1 * | 1/2004 | Vonesh | A61F 2/07 623/1.11 |
| 6,673,105 B1 | 1/2004 | Chen | |
| 6,780,497 B1 | 8/2004 | Walter | |
| 6,863,686 B2 | 3/2005 | Shannon et al. | |
| 6,878,161 B2 | 4/2005 | Lenker | |
| 6,890,350 B1 | 5/2005 | Walak | |
| 6,899,727 B2 | 5/2005 | Armstrong | |
| 6,929,659 B2 * | 8/2005 | Pinchuk | A61F 2/07 623/1.13 |
| 6,945,994 B2 * | 9/2005 | Austin | A61F 2/91 623/1.15 |
| 7,056,336 B2 * | 6/2006 | Armstrong | A61F 2/07 623/1.13 |
| 7,083,640 B2 * | 8/2006 | Lombardi | A61F 2/07 623/1.18 |
| 7,090,695 B2 * | 8/2006 | Solem | A61F 2/2451 128/898 |
| 7,118,600 B2 * | 10/2006 | Dua | A61F 2/04 623/23.68 |
| 7,288,111 B1 * | 10/2007 | Holloway | A61F 2/86 623/1.13 |
| 7,547,321 B2 * | 6/2009 | Silvestri | A61F 2/91 623/1.15 |
| 8,062,354 B2 | 11/2011 | Shannon et al. | |
| 8,764,813 B2 * | 7/2014 | Jantzen | A61F 2/07 623/1.13 |
| 8,784,473 B2 * | 7/2014 | Tupil | A61F 2/07 623/1.12 |
| 8,888,836 B2 * | 11/2014 | Berglund | A61F 2/91 623/1.12 |
| 9,364,354 B2 * | 6/2016 | Ben-Muvhar | A61B 17/12036 |
| 2002/0177890 A1 * | 11/2002 | Lenker | A61F 2/90 623/1.12 |
| 2003/0045923 A1 * | 3/2003 | Bashiri | A61F 2/91 623/1.12 |
| 2003/0074049 A1 * | 4/2003 | Hoganson | A61F 2/07 623/1.13 |
| 2003/0195609 A1 * | 10/2003 | Berenstein | A61F 2/856 623/1.15 |
| 2003/0236566 A1 * | 12/2003 | Heuser | A61F 2/07 623/1.12 |
| 2004/0186551 A1 * | 9/2004 | Kao | A61F 2/91 623/1.15 |
| 2005/0004647 A1 * | 1/2005 | Bassoe | A61F 2/958 623/1.11 |
| 2005/0090888 A1 | 4/2005 | Hines et al. | |
| 2007/0233270 A1 | 10/2007 | Weber et al. | |
| 2008/0119943 A1 * | 5/2008 | Armstrong | A61F 2/89 623/23.7 |
| 2009/0234432 A1 * | 9/2009 | Pacetti | A61F 2/91 623/1.16 |
| 2009/0319023 A1 * | 12/2009 | Hildebrand | A61F 2/07 623/1.13 |
| 2010/0312326 A1 | 12/2010 | Chuter et al. | |
| 2013/0172982 A1 * | 7/2013 | Pacetti | A61F 2/915 623/1.15 |
| 2013/0253426 A1 | 9/2013 | Campbell | |

FOREIGN PATENT DOCUMENTS

| | | |
|---|---|---|
| EP | 1 582 181 | 10/2005 |
| WO | WO-2000042947 A2 | 7/2000 |
| WO | 01/45766 | 7/2001 |
| WO | 2004/000375 | 12/2003 |
| WO | WO-2004000375 A1 | 12/2003 |
| WO | WO-2012122023 A2 | 9/2012 |

OTHER PUBLICATIONS

European Search Report from EP17207506.1, dated Jul. 24, 2018, 9 pages.

* cited by examiner

SELF-EXPANDING, BALLOON EXPANDABLE STENT-GRAFTS

FIELD OF THE INVENTION

The present invention relates to the field of self-expandable stent-grafts that are further additionally balloon expandable.

BACKGROUND OF THE INVENTION

Various commercial articles have been manufactured from porous materials having fibrillar microstructures including various implantable medical devices. Examples of these materials may include porous expanded polytetrafluoroethylene (ePTFE) and stretched polyethylenes and polypropylenes. Articles fabricated from these porous fibrillated materials include fabrics, battery membranes, various filters, electrical insulation and various medical devices including vascular grafts, tissue repair patches, sutures and stent-grafts. Porous materials used to manufacture articles such as these can take the form of, for example, sheets, thin films and tubes. It is known that nominal physical dimensions of some of these articles may be changed (reduced) by applying compressive forces to these materials, particularly in a direction substantially parallel to the predominant direction of the fibrils. Compressive forces applied to these materials result in a decrease in porosity (i.e., an increase in bulk density; a decrease in the volume of void space) as the material is moved into the available void space due to the compressive force. Compressive forces applied to these fibrillar materials in directions substantially parallel to the general directional orientation of the fibrils will result in bending of the previously substantially straight fibrils. The compressed material may then be heated for suitable time and temperature so that the bent form of the fibrils becomes permanent. Fibrillar materials so processed to have these formed bent fibrils are typically extensible by applied tensile force in a direction generally parallel to the directional orientation of the fibrils. Upon release of the tensile force, these materials will typically recover most or all of the extended length. The use of compression to form bent fibrils in fibrillated materials is taught in U.S. Pat. No. 5,308,664 to House and Myers.

It is also known to apply coatings of various materials to fibrillated polymeric substrates for a variety of purposes. Thermoplastic coatings on such substrates are sometimes used as adhesives for bonding together different components of an article. A thermoplastic coating of fluorinated ethylene propylene (FEP) applied to ePTFE, for example, is taught by U.S. Pat. No. 5,735,892 to Myers et al.

For some applications, however, it may be advantageous for a product to remain at the partially or fully extended dimension following release of the extending tensile force. A fracturable coating applied to a porous substrate material having a microstructure of bent fibrils may be used to create an article that can be, during normal use, permanently increased in at least one dimension by the application of a tensile force.

SUMMARY OF THE INVENTION

A coating applied to fibrillated porous materials having bent fibrils is described that allows a size dimension of an article fabricated from such a material to be permanently increased by the application of an extending force. One suitable precursor porous substrate material is ePTFE that has been compressed in a direction substantially parallel to a direction of orientation of the fibrils generally as taught by U.S. Pat. No. 5,308,664 to House and Myers, incorporated by reference herein in its entirety. The coating may be any material that solidifies to provide a material that is fracturable under the deliberate application of a tensile force during normal use of the article (e.g., solvent-based coatings). The coating may be applied before or after bending of the fibrils. Particularly for use with ePTFE substrates, the coating may be, for example, a thermoplastic polymeric material and more particularly may be a thermoplastic fluoropolymer such as FEP.

Coating materials may be applied to one or both surfaces of a porous fibrillated substrate material or alternatively may be impregnated into void spaces of the substrate. Some degree of impregnation may occur with coatings that are applied to the substrate surfaces. Coating materials other than thermoplastic materials may include, for example, various polyimides. The amount of coating material and the coating thickness will need to be determined based on the requirements of the article being manufactured.

Articles made as taught herein may be in the form of sheets, rods, tubes or any other form that may benefit from being made to be extensible in at least one direction. One way of making a sheet article is to take a length of a tube and cut it lengthwise through its wall thickness.

The fibrils of the substrate material are required to be bent, generally as taught by U.S. Pat. No. 5,308,664. The presence of bent fibrils provides the substrate material with extensibility in the direction of orientation of the fibrils; i.e., the length of the material may be extended progressively until the bent fibrils are pulled out to a substantially straight configuration. When a fibrillated porous substrate such as described herein is provided with a suitable fracturable coating (constraining the fibrils in their bent form), it may be extended in the general direction of orientation of the fibrils by the application of an extending force sufficient to fracture the coating material to thereby allow at least one dimension of the material to be extended by straightening of the bent fibrils.

Substrate materials such as ePTFE may be provided with a covering or wrapping of a thin film such as ePTFE film. The film may be joined to a substrate layer so that the predominant direction of orientation of fibrils within the film is oriented in a different direction to the predominant direction of fibrillar orientation of the substrate; likewise, the fibrillar orientations of these two layers may be in the same direction. Such laminates of film and substrate may be provided with bent fibrils in either the substrate layer, the film layer or both layers. It is also apparent that laminates may include multiple layers of film (with individual layers oriented as desired) without a different (from the film) substrate layer. The use of film and substrate laminates is known with ePTFE materials. A particularly useful ePTFE film for the manufacture of articles as described herein is taught by U.S. Pat. No. 5,476,589 to Bacino, incorporated by reference herein in its entirety.

The coated materials described herein are anticipated to be particularly useful for implantable medical devices such as vascular grafts and stent-grafts when it may be desirable for a medical practitioner to be able to permanently increase the length, the diameter or both the length and the diameter of such devices. For length extension, the extending force is a longitudinally oriented tensile force that may be applied by hand. For diameter increases, typically the extending force would be applied by inflation of a catheter balloon within the lumen of a device. While a balloon exerts an outward force in a direction against the wall thickness of a tubular device, that outward force translates into a circumferentially oriented tensile force to cause straightening of circumferentially oriented bent fibrils and fracturing of the fracturable coating material.

Grafts, and particularly tubular grafts, made as described herein, can allow for customization of device diameter to match the vessel treatment zone. Tapered vessels may be treated more easily. Risk of infolding of graft material due to an overly large diameter graft being fitted within a smaller vessel is reduced or eliminated, thus providing a substantially wrinkle-free lumen. The number of device sizes required to treat a patient population can be reduced because a given device made as taught herein can be used to treat a larger range of vessel sizes than devices made with more conventional technologies. Various applications of such devices may include stent-grafts for peripheral applications and for aneurismal repair, stent-grafts provided on one or both ends of a vascular graft for dialysis, pediatric shunts and hepatic grafts. It is also noteworthy that the radial force of a self-expanding stent-graft against a vessel wall is minimized by the use the fracturable coating described herein to constrain the self-expanding stent-graft rather than the self-expanding stent being constrained by the vessel.

Stent-grafts made as taught herein may be compacted to a small diameter after manufacture and constrained at that diameter by, for example, providing a removable constraining sheath. After such a device is inserted through a vasculature (typically transported via a catheter) to a desired deployment site, the stent-graft may be deployed by removal of the constraining sheath, which allows the graft to self-expand to an enlarged first diameter. The device may be manufactured to include flared ends of maximum diameter larger than the enlarged first diameter to which the body of the stent-graft (excluding the ends) expands during deployment. These flared ends are useful for retaining the device at the desired deployment site with little or no risk of unintended migration. The stent-graft may then be mechanically expanded as desired up to a still larger, maximum second diameter by, for example, the use of a catheter balloon. Typically, this still larger, maximum second diameter is equal to about the maximum diameter of the flared end(s). Said another way, the maximum diameter of the flared end(s) is the same as the still larger, maximum second diameter to which the device may be balloon expanded, meaning that the "flare" of the flared end disappears into the larger, maximum second diameter to which the device has been balloon expanded. The flared end(s) do not increase in maximum diameter as the device is balloon expanded.

Any of these graft products may also be provided with therapeutic agents known in the art (e.g., anti-clotting agents). For some applications, a therapeutic agent may be incorporated with the fracturable coating. Other applications may involve the application of a therapeutic agent to an uncoated surface of the fibrillated substrate, e.g., directly to an ePTFE surface.

A method of making such devices (as will be further described) involves the use of a tubular fibrillated substrate (e.g., a longitudinally extruded and expanded ePTFE tube having fibrils that are oriented in a direction substantially parallel to the longitudinal axis of the tube) that has been wrapped with a thin fibrillated film. Wrapping is most easily accomplished by first temporarily placing the substrate tube onto a mandrel. The wrapping is preferably a helical wrap using a film that has been cut into a tape, with the predominant direction of orientation of the fibrillar microstructure of the film being parallel to the length of the tape. The tape will have been provided with a coating of a fracturable material prior to the wrapping step. This fracturable material may also serve as an adhesive to adhere the wrapped tape to the substrate tube, in which case the wrapping will be performed with the coated side of the tape facing the substrate. If the coating is a thermoplastic material, the wrapped substrate tube (still on the temporary mandrel) may be heated sufficiently to cause the coating to melt to an extent to ensure adhesion between the tape and the substrate. The mandrel may be removed following the heating step.

If a longitudinally extensible device is desired, then the substrate tube should be provided with bent fibrils that are primarily longitudinally oriented. If a diametrically extensible device is desired then following the application of the helically wrapped film, the diameter of the device is compacted (i.e., reduced) to cause the circumferentially oriented fibrils of the film to become bent. The compacting force is essentially a compressive force. This compacting may be accomplished prior to or during the above-described heating step. It is also possible to make such a device having both longitudinally and circumferentially oriented bent fibrils that is extensible both longitudinally and horizontally.

An alternative method entails modifying a fibrillated porous material having a microstructure of nodes interconnected by fibrils, by applying compression to the material in a direction parallel to the orientation of the length of the nodes in an amount sufficient to cause buckling and folding of the nodes. This is preferably accomplished in a manner that does not result in macroscopically visible wrinkling of the material. Heat may be applied to the material after the nodes have been folded sufficient to set the form of the folded nodes. Such a material may subsequently be extended in the direction of the length of the nodes back to about its pre-compressed dimension, by the application of a sufficient tensile force.

U.S. Pat. No. 6,336,937 to Vonesh et al. entitled Multistage Expandable Stent-graft teaches a method of making stent-grafts that are self-expanding devices that may be subsequently adjusted to a still larger diameter with a catheter balloon. While the method of this patent is different from the method taught herein, U.S. Pat. No. 6,336,937 is incorporated by reference herein in its entirety.

DETAILED DESCRIPTION OF THE INVENTION

As described above, for the manufacture of extensible medical devices such as vascular grafts and stent-grafts, ePTFE films are preferred for use with ePTFE substrates. A preferred fracturable coating for these ePTFE films (particularly for implantable medical devices) is FEP. The FEP-coated porous expanded PTFE film described herein was made by a process which comprises the steps of:

a) contacting a porous PTFE film with another layer which is preferably a film of FEP or alternatively of another thermoplastic polymer;

b) heating the composition obtained in step a) to a temperature above the melting point of the thermoplastic polymer;

c) stretching the heated composition of step b) while maintaining the temperature above the melting point of the thermoplastic polymer; and d) cooling the product of step c).

In addition to FEP, other thermoplastic polymers including thermoplastic fluoropolymers may also be used to make this coated film. The coating on the porous expanded PTFE film may be either continuous (non-porous) or discontinuous (porous) depending primarily on the amount and rate of stretching, the temperature during stretching, and the thickness of the adhesive prior to stretching. The coated films may be easily cut into tapes for wrapping tubular substrates.

The discontinuously FEP-coated porous expanded PTFE film used to construct the devices described herein (unless specifically described otherwise) was of about 0.025 mm thickness. The ePTFE portion of this coated film had a bulk density of about 0.6 g/cc; the film chosen was an ePTFE film made generally as taught by U.S. Pat. No. 5,476,589 to Bacino.

The following scanning electron photomicrographs are provided as an overview of materials chosen to manufacture examples described herein. The images depict these materials at various stages of manufacture of a stent-graft and also illustrate the effects of subsequent balloon expansion on the materials of the completed stent-graft. The photomicrographs are oriented so that the longitudinal axis of the illustrated tubular structure is horizontal when viewing the photomicrographs with the label at the lower edge.

Figure 1:
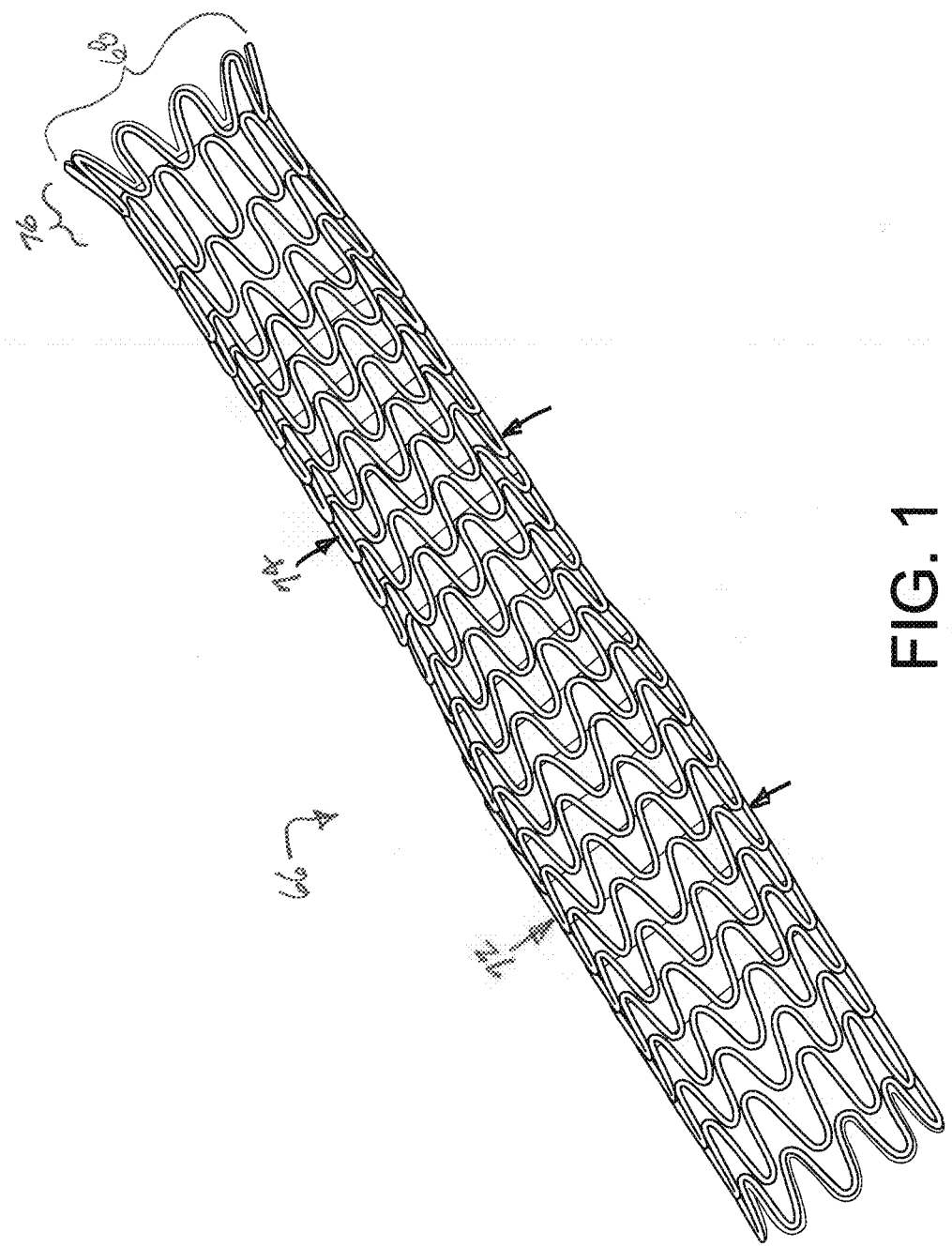
FIG. 1 is a side view of a stent-graft of about 5 cm length made as described herein; about one half of the length of the device has been expanded by a catheter balloon from an inside diameter of 4 mm to an inside diameter of 6 mm.

FIG. 1 is a side view of a stent-graft of about 5 cm length made as described herein; about one half of the length of the device has been expanded by a catheter balloon from an inside diameter of 4 mm to an inside diameter of 6 mm.

Figure 2:
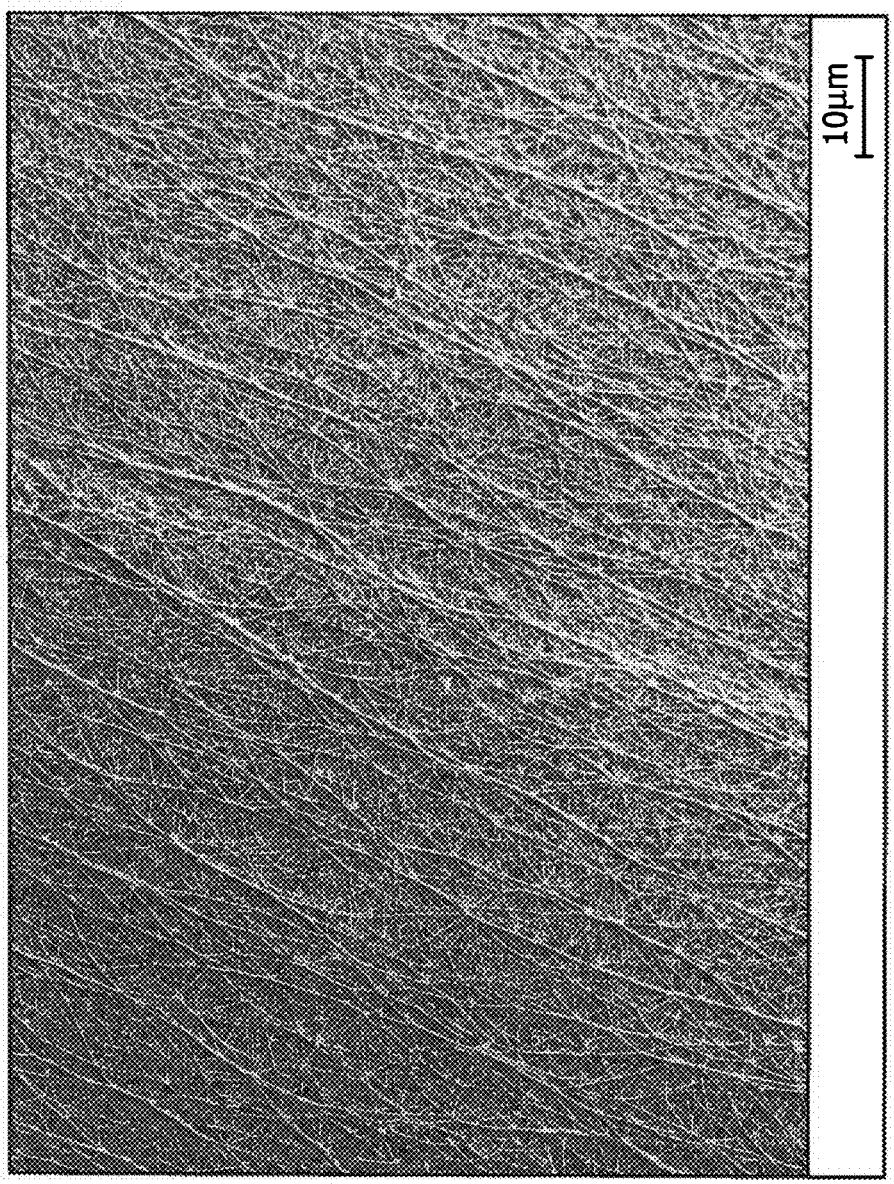
FIG. 2 is a scanning electron photomicrograph of the ePTFE side of an FEP-coated ePTFE film used to make devices described herein.

FIG. 2 is a scanning electron photomicrograph of the ePTFE side of a FEP-coated ePTFE film used to make devices described herein, using FEP-coated ePTFE film as described above.

Figure 3:
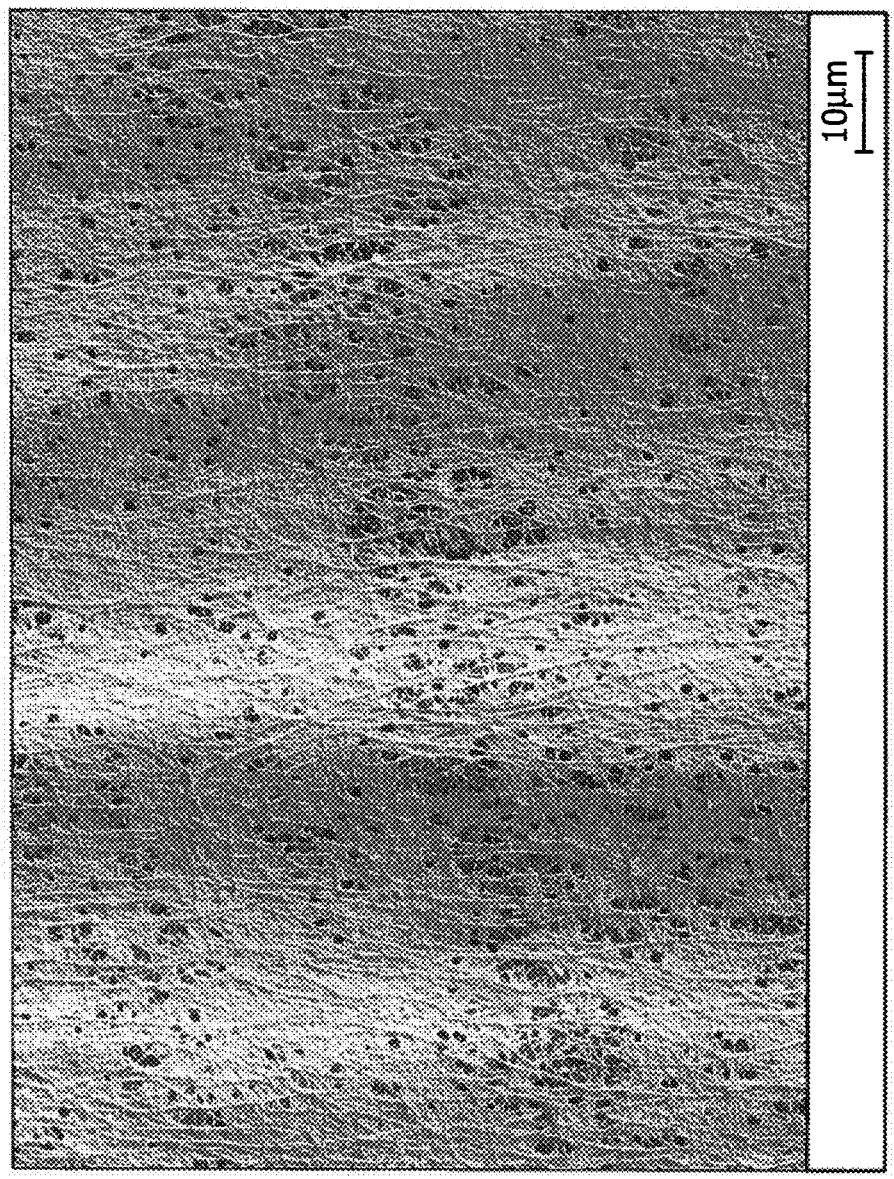
FIG. 3 is a scanning electron photomicrograph of the FEP coated side of the FEP-coated ePTFE film used to make devices described herein.

FIG. 3 is a scanning electron photomicrograph of the film shown in FIG. 2, showing the opposite, discontinuously FEP coated side of the FEP-coated ePTFE film.

Figure 4:
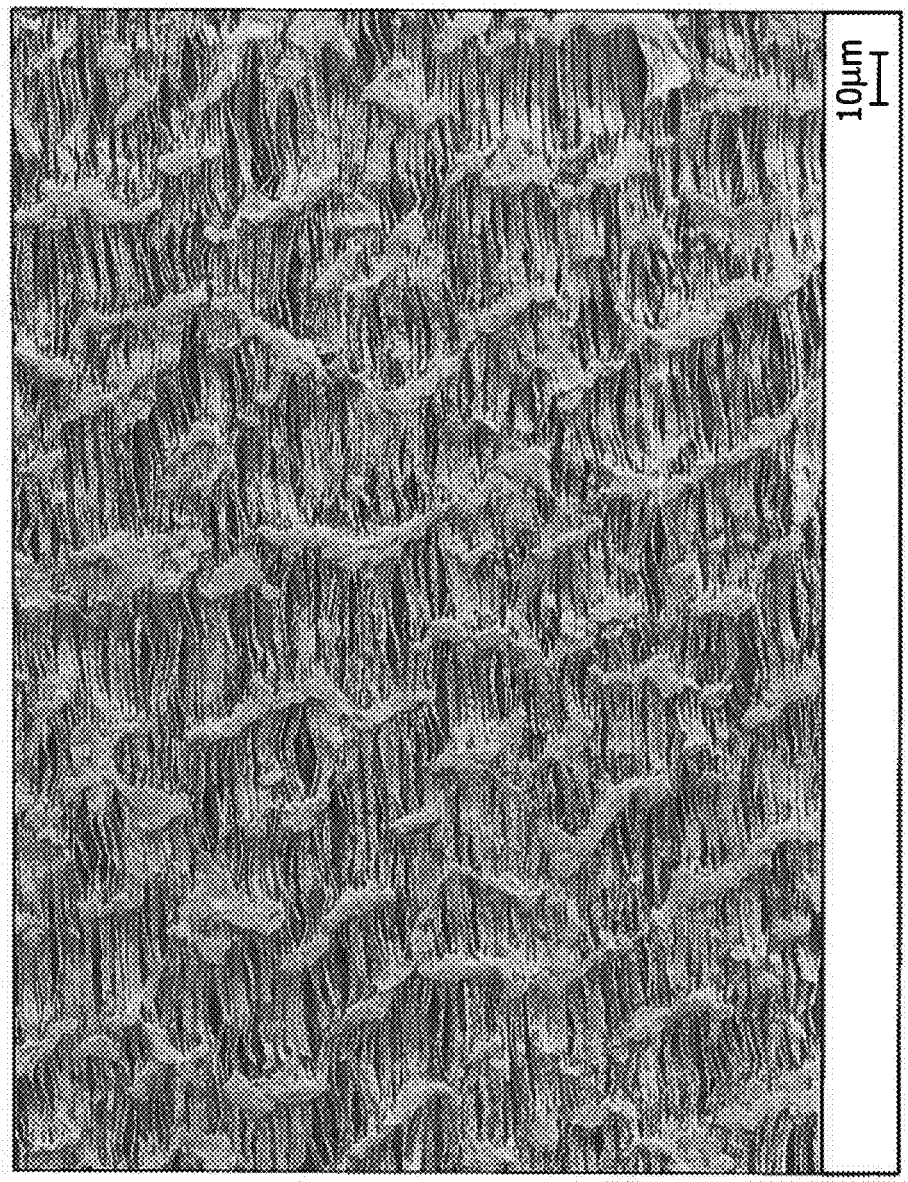
FIG. 4 is a scanning electron photomicrograph of the luminal surface of a 6 mm inside diameter ePTFE substrate tube as used to make a stent-graft described herein.

FIG. 4 is a scanning electron photomicrograph of the luminal surface of a 6 mm inside diameter ePTFE substrate tube as used to make a stent-graft described herein.

Figure 5:
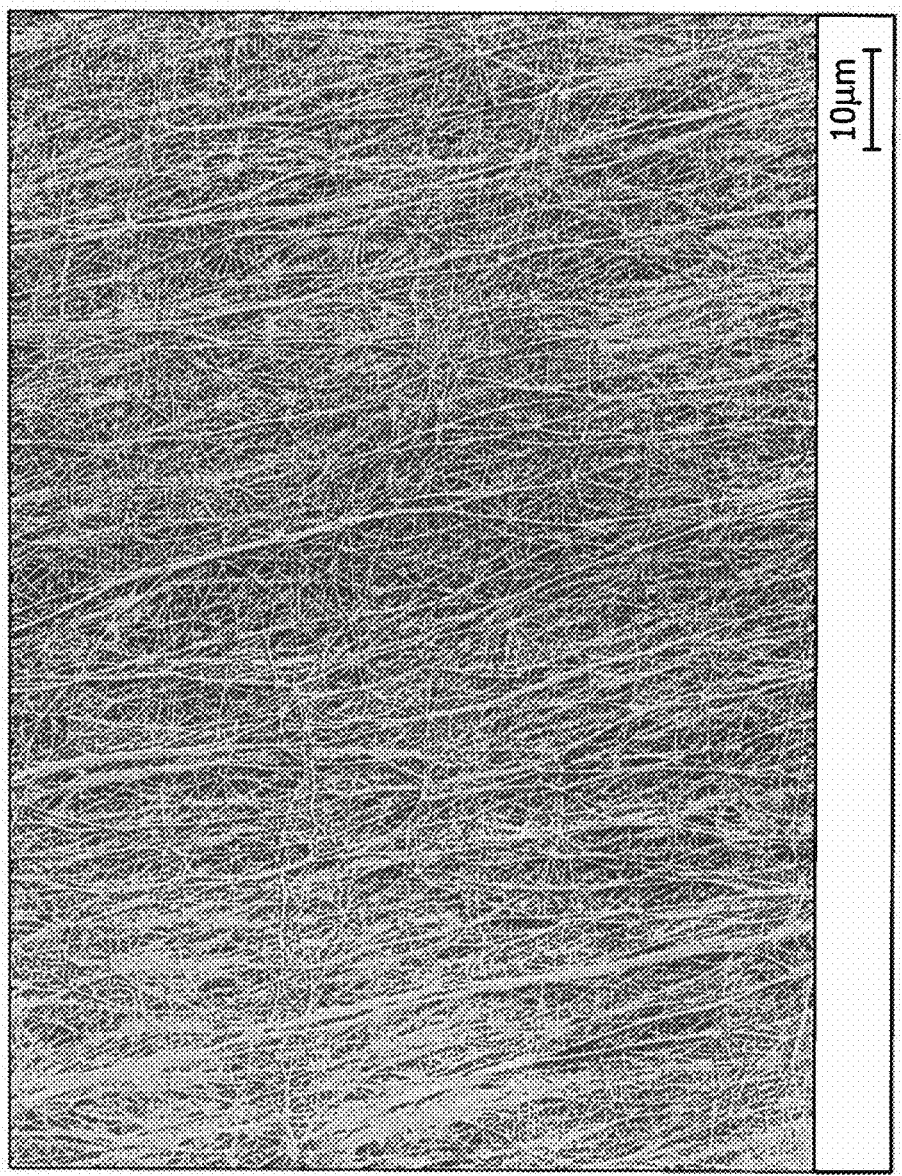
FIG. 5 is a scanning electron photomicrograph of the abluminal surface of the ePTFE substrate tube of FIG. 4 that has been helically wrapped with the FEP-coated ePTFE film applied with the FEP facing the substrate tube.

FIG. 5 is a scanning electron photomicrograph of the abluminal surface of the ePTFE substrate tube of FIG. 4 that has been helically wrapped with the FEP-coated ePTFE film applied with the FEP facing the substrate tube.

Figure 6:
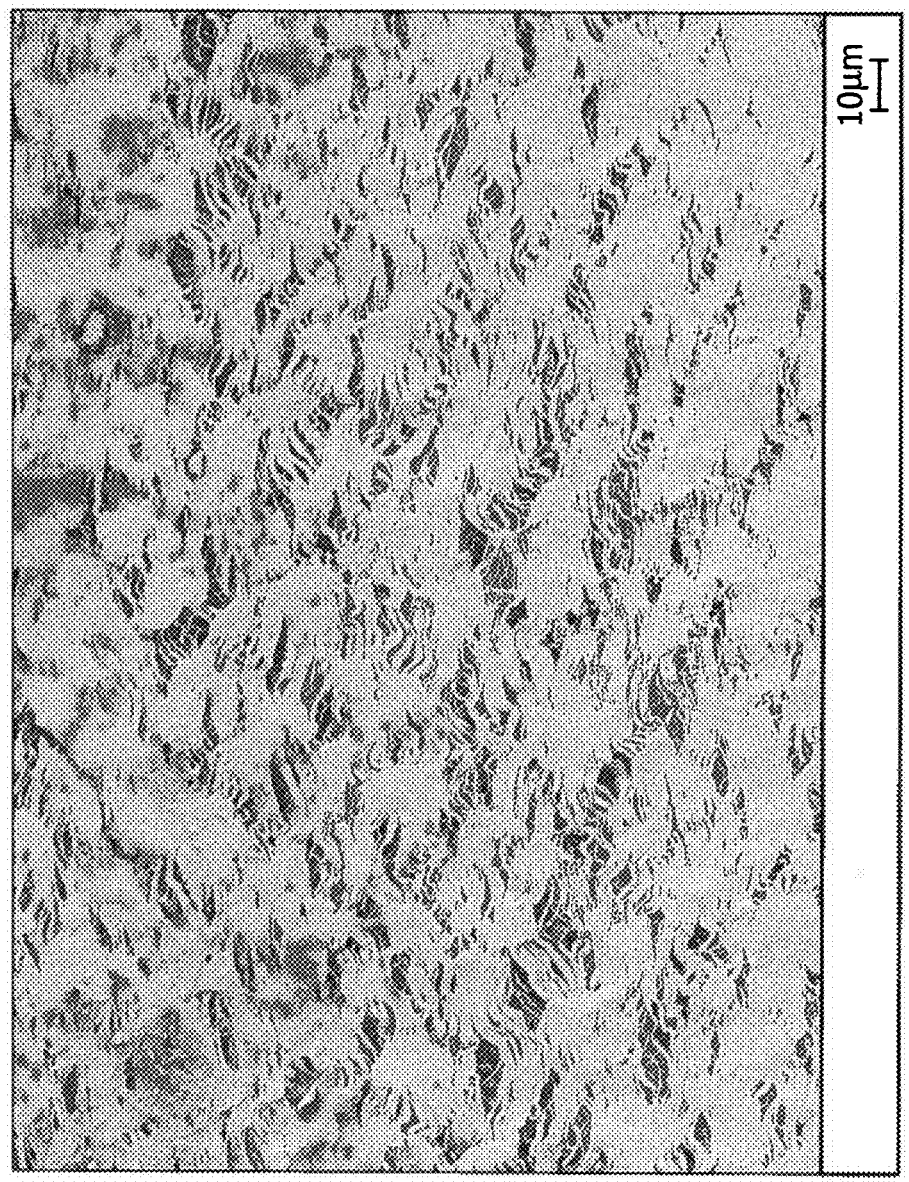
FIG. 6 is a scanning electron photomicrograph of the luminal surface of an ePTFE substrate tube as used to make a stent-graft described herein, following compaction of the stent-graft (with radial compression and heat) to an inside diameter of 4 mm.

FIG. 6 is a scanning electron photomicrograph of the luminal surface of an ePTFE substrate tube as used to make a stent-graft described herein, following compaction of the stent-graft (with radial compression and heat) to an inside diameter of 4 mm.

Figure 7:
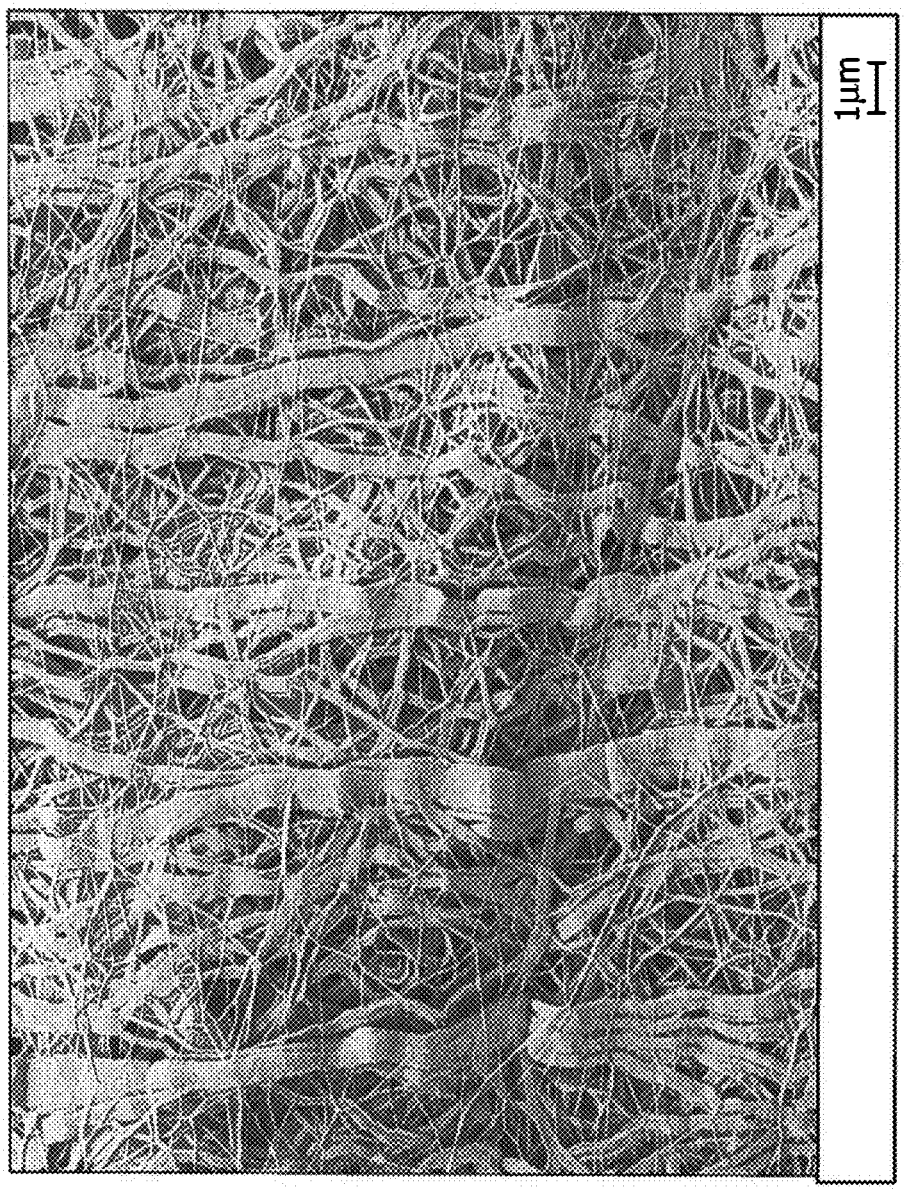
FIG. 7 is a scanning electron photomicrograph of the abluminal surface of the ePTFE substrate tube as used to make a stent-graft described herein, following compaction (with radial compression without applied heat (atypical, for illustration only)) to an inside diameter of 4 mm, showing that the FEP has not interpenetrated through the ePTFE film to the outer surface of that film.

FIG. 7 is a scanning electron photomicrograph of the abluminal surface of the film-wrapped ePTFE substrate tube as used to make a stent-graft described herein, following compaction (with radial compression without applied heat (atypical, for illustration only)) to an inside diameter of 4 mm, showing the bent fibrils of the film and showing that the FEP has not interpenetrated through the ePTFE film to the outer surface of that film.

Figure 8:
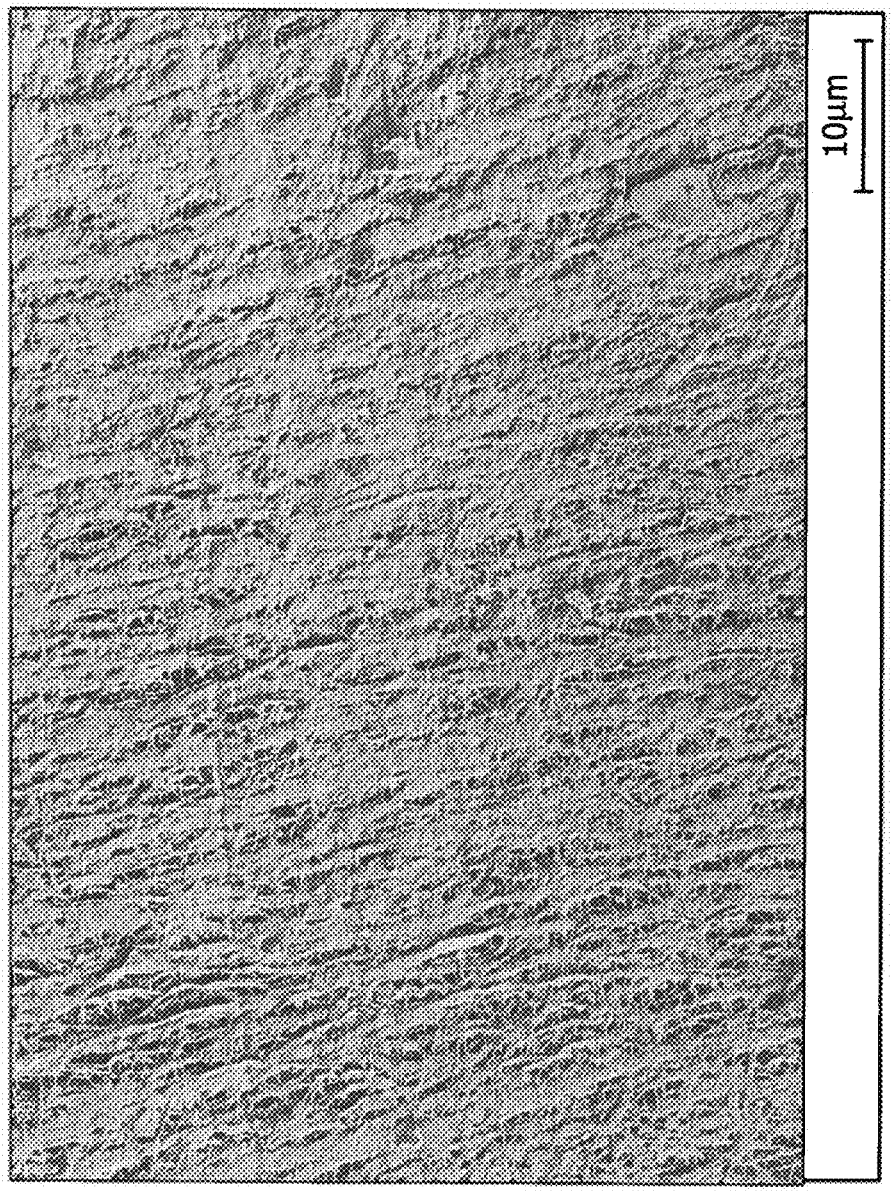
FIG. 8 is a scanning electron photomicrograph of the abluminal surface of the ePTFE substrate tube as used to make a stent-graft described herein, following compaction (with radial compression and with applied heat (typical)) to an inside diameter of 4 mm, showing the interpenetration of the FEP through the ePTFE film to the outer surface of that film.

FIG. 8 is a scanning electron photomicrograph of the abluminal surface of the film-wrapped ePTFE substrate tube as used to make a stent-graft described herein, following compaction (with radial compression and with applied heat (typical)) to an inside diameter of 4 mm, showing the interpenetration of the FEP through the ePTFE film to the outer surface of that film.

Figure 9:
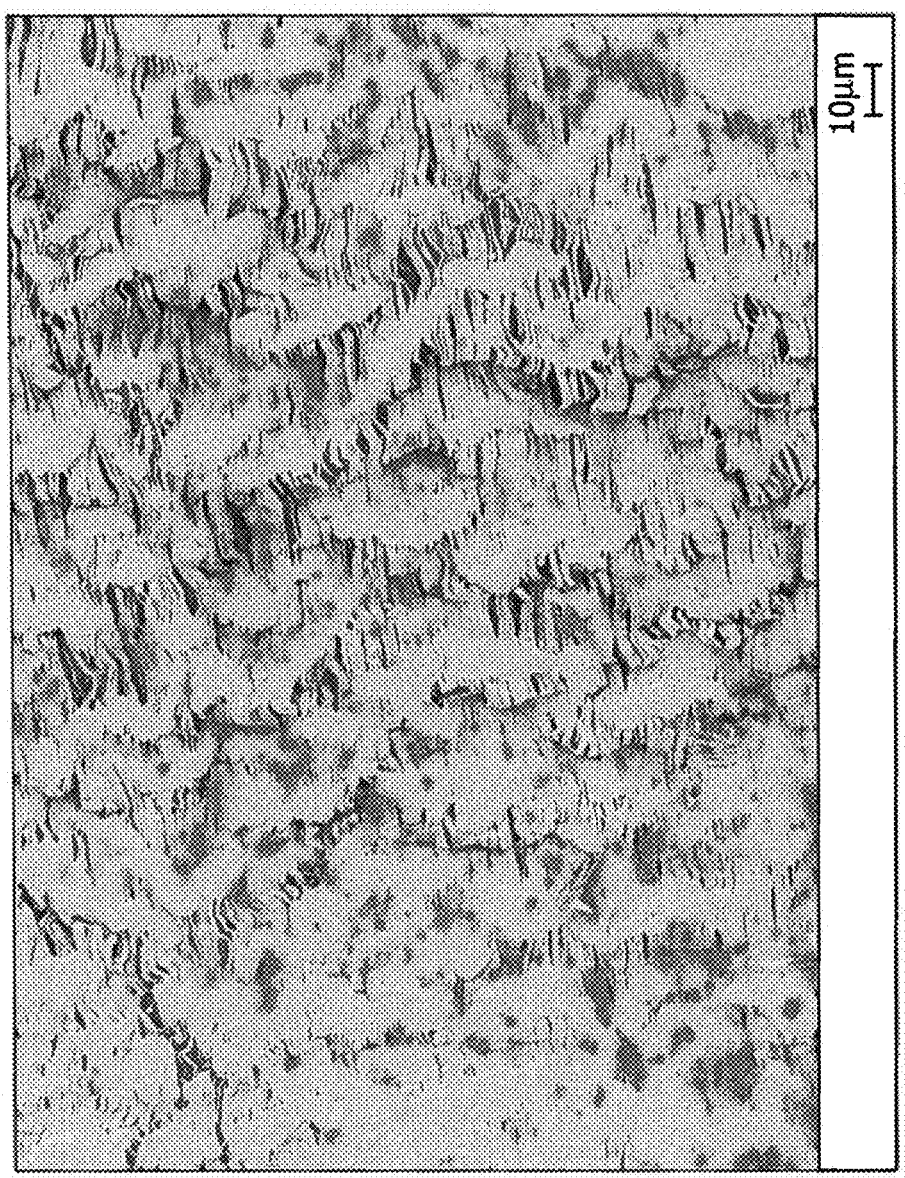
FIG. 9 is a scanning electron photomicrograph of the luminal surface of an ePTFE substrate tube as used to make a stent-graft described herein, following compaction of the stent-graft (with radial compression and heat) to an inside diameter of 4 mm in turn followed by expansion of the stent-graft with a catheter balloon to an inside diameter of 6 mm.

FIG. 9 is a scanning electron photomicrograph of the luminal surface of an ePTFE substrate tube as used to make a stent-graft described herein, following compaction of the stent-graft (with radial compression and heat) to an inside diameter of 4 mm in turn followed by expansion of the stent-graft with a catheter balloon to an inside diameter of 6 mm.

Figure 10:
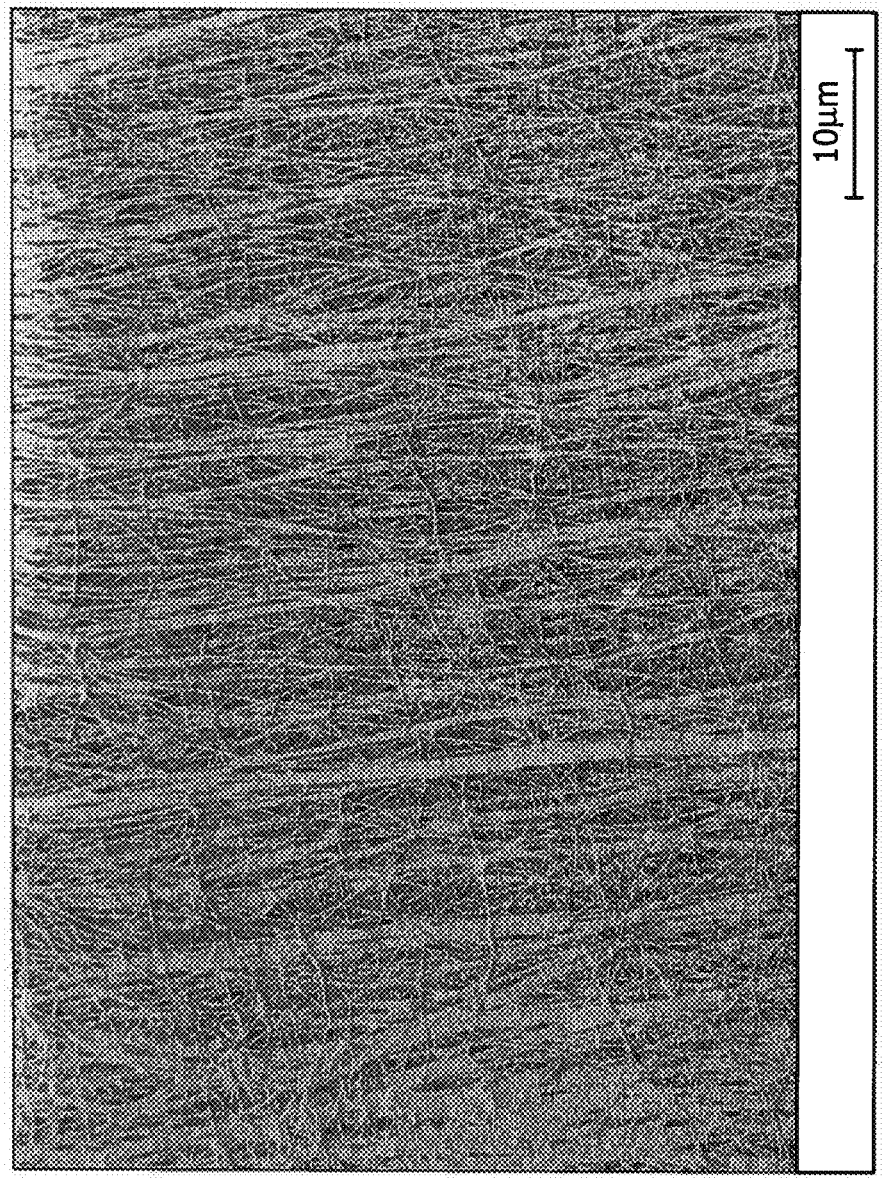
FIG. 10 is a scanning electron photomicrograph of the abluminal surface of the stent-graft shown in FIG. 9.

FIG. 10 is a scanning electron photomicrograph of the abluminal surface of the stent-graft shown in FIG. 9.

Example 1: Diametrically Adjustable Vascular Graft

Figure 11:
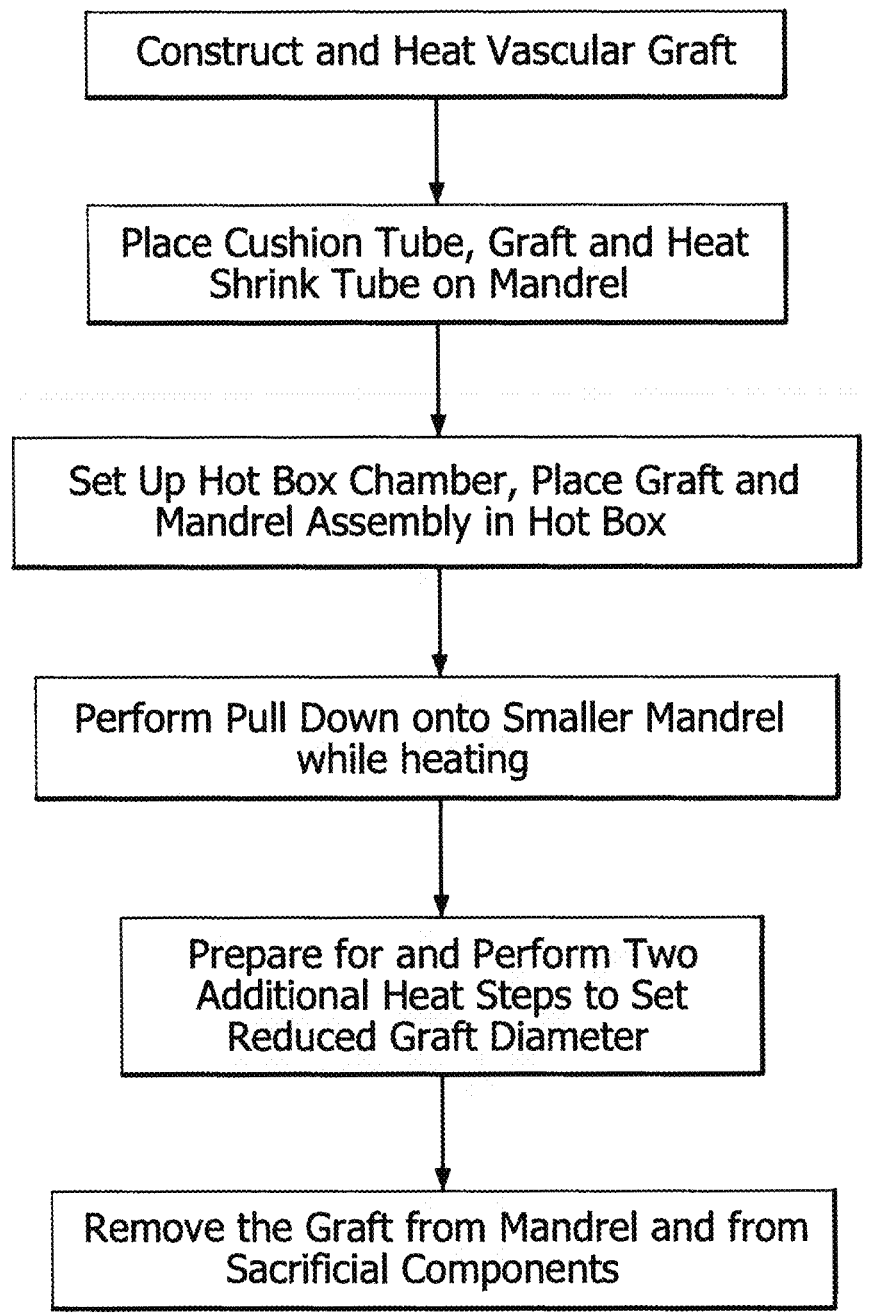
FIG. 11 describes a flow chart for the basic steps involved in the manufacture of a diametrically extensible ePTFE vascular graft.

The following is a description of a method used to make a diametrically extensible vascular graft that may be increased in diameter by inflation of a catheter balloon placed temporarily within the lumen of the vascular graft. The method described for making of the balloon extensible vascular graft is similar to a method described below for making of a balloon extensible stent-graft. The example of the vascular graft described herein was made to be diametrically extensible from a 4 mm inside diameter to a 6 mm inside diameter; larger ranges of extensibility are possible. A flow chart summary of this manufacturing process is described by FIG. 11.

First, a longitudinally extruded and expanded ePTFE tube was obtained, the tube having a 6 mm inside diameter, 15 cm length, 0.6 mm wall thickness and approximate 22 micron mean fibril length. This tube was fitted over a 6 mm outside diameter (OD) stainless steel mandrel. The tube was then provided with a helical wrap of 4 layers of 12.7 mm wide film of the type described above, with the FEP-coated side of the film against the outer surface of the ePTFE tube. Many of the fibrils of the film were thus substantially circumferentially oriented with respect to the mandrel and the ePTFE substrate tube.

The assembly was placed in a convection oven set at 320° C. for 20 minutes. This was sufficient heat to cause the FEP coating on the film to begin to melt, resulting in adhesion of the film to adjacent film layers and to the underlying ePTFE substrate tube, thereby creating, for purposes of this description, a vascular graft.

Next, a 6 mm OD tubular stainless steel mandrel was obtained, the mandrel having a 4 mm inside diameter (ID) and a slight (4°) taper (measured from the longitudinal axis of the mandrel) from the OD to the ID on one end. A 4 mm OD mandrel was inserted into the tapered end of the 6 mm mandrel, the 4 mm mandrel being sized to be a slip fit within the lumen of the 6 mm mandrel. (Alternatively, an adjustable diameter mandrel may be used.) A sacrificial thin wall ePTFE 5 mm ID cushion tube (30 cm length, 0.1 mm wall thickness, approximate 22 micron mean fibril length) was fitted onto the 6 mm mandrel with one end extending beyond the tapered end of the 6 mm mandrel about 5 cm onto the 4 mm mandrel. The previously created vascular graft was then fitted onto the 6 mm mandrel over the cushion tube, about 3 cm back from the taper. A length of sacrificial FEP shrink tube (Zeus Industrial Products, Inc., Orangeburg S.C.) having about a 1.6:1 ratio of expanded to retracted diameter was then fitted over the graft, the shrink tube being sized for clearance over the graft and having a length greater than that of the graft. The various components fitted onto the mandrel comprise the "assembly" that was subsequently processed.

A cylindrical hot box chamber of about 2.5 cm length with opposing round openings of about 9.5 mm on the entrance and 7.9 mm on the exit was attached to a heat source (Balloon Development Station Model 210-A, Beahm Designs, Los Gatos Calif.) set to 240° C. The opening sizes of the hot box chamber were chosen to provide clearance over the assembly on the 6 and 4 mm mandrels respectively. The tapered end of the 6 mm mandrel was placed in the center of the hot box chamber with the 4 mm mandrel extending out of the smaller chamber end. The location of the 6 mm mandrel was fixed in order to keep the tapered end of the 6 mm mandrel centered in the hot box.

The cushion tube and the 4 mm mandrel were grasped and both were pulled together through the hot box. Pulling was accomplished at a rate appropriate to shrink the FEP shrink tube tightly as it moved down the taper. As the vascular graft and shrink tube entered the chamber, the shrink tube collapsed onto the outside of the vascular graft. The graft moved down the taper onto the 4 mm mandrel, contained on the inside by the taper and on the outside by the shrink tube as it continued to reduce in diameter. This resulted in the microscopic bending of the fibrils in the helically wrapped film while avoiding macroscopic folding of the graft.

Following shrinking of the heat shrink tubing onto the vascular graft assembly and the 4 mm mandrel, the assembly was heated in a convection oven set at 210° C. for 10 minutes. This step was intended to heat set the bent fibrils. Next, the FEP shrink tubing was removed from the assembly. The vascular graft was then helically overwrapped with a sacrificial layer of 0.13 mm thick skived PTFE tape (St. Gobain Performance Plastics, Paris, France), after which the ends of the sacrificial ePTFE cushion tube extending beyond the ends of the vascular graft were cut off using a sharp blade. The assembly still on the 4 mm mandrel was placed in a convection oven set at 320° C. for ten minutes, causing the FEP coating on the ePTFE film to melt and flow into and at least partially through the bent fibrils of the film.

The graft assembly was then removed from the 4 mm mandrel, and the sacrificial skived PTFE wrapping and cushion tube were then removed from the vascular graft. Due to the FEP bonds holding the fibrils in the wrapped film in their bent configuration, the graft thus prepared remained at 4 mm ID until an internal force was introduced to increase its diameter. To test the graft, a 6 mm catheter balloon attached to a balloon inflator via its catheter was inserted into the graft and inflated. The graft gradually increased in diameter until returned to its original 6 mm diameter at about 7 atmospheres of balloon inflation pressure.

Example 2: Self Expanding/Balloon Adjustable Stent-Graft

A 4 mm covered stent-graft with a self-expanding nitinol wire stent (a helically wound serpentine wire form) that can be subsequently extended in diameter (e.g., with a catheter balloon) to 6 mm was made as described below; this stent-graft is illustrated in FIG. 1 which shows a portion of the stent-graft having been balloon expanded to an ID of 6 mm.

An ePTFE tube was obtained, the tube having a 6 mm ID, about 8 cm length, bulk density of about 0.6 g/cc, 0.1 mm wall thickness and approximate 22 micron mean fibril length. This tube was fitted over a 6 mm OD stainless steel mandrel, then wrapped with FEP-coated ePTFE film and heated as described above for the example of the diametrically extensible vascular graft. The graft was then removed from the 6 mm OD stainless steel mandrel. An ePTFE sacrificial cushion tube as described previously was fitted onto a 6 mm OD porous stainless steel mandrel, after which the film-wrapped ePTFE graft was fitted over the cushion tube.

A helically wound wire stent was obtained and then fitted over the center of the length of the film-wrapped ePTFE tube at a stent length of about 5 cm. 1 mm wide FEP-coated film, about 0.01 mm FEP thickness, about 0.035 mm total thickness, bulk density about 1.2 g/cc was then wrapped over the length of the helically wound wire, centered on the width of the serpentine form so that the apices of the serpentine form remained exposed. A 12.7 mm wide strip of this film was then wrapped circumferentially around each end of the device covering about the last three windings of the helical wire form. This film extended beyond the end of the stent. An overwrapping of sacrificial skived PTFE tape was then applied over the entire length of the stent. The resulting assembly was then placed into a convection oven set at about 320° C. A vacuum was applied to the lumen of the porous mandrel and the assembly was left in the oven to heat for 10 minutes, after which the assembly was removed and allowed to cool to about ambient temperature.

The resulting stent-graft was removed from the 6 mm porous mandrel and the cushion tube removed from the lumen of the now-formed stent-graft. The stent-graft was then fitted onto another 6 mm OD stainless steel mandrel and the film protruding beyond the ends of the stent was trimmed with a laser (Blockwise Engineering, Tempe Ariz.) to conform to the serpentine wire. The trimmed stent-graft was then removed from the 6 mm mandrel.

A 6 mm mandrel having one tapered end and including a 4 mm OD mandrel inserted into the tapered end of the lumen of the 6 mm mandrel was obtained, (this mandrel previously described above). A sacrificial ePTFE inner cushion tube (also as the previously described cushion tube) was fitted onto the 6 mm mandrel, extending about 5 cm onto the 4 mm mandrel. The stent-graft was then fitted over the portion of the cushion tube covering the 6 mm mandrel to about 3 cm from the beginning of the taper.

A sacrificial helical wrapping of skived PTFE tape (St. Gobain Performance Plastics, Paris, France) was then applied over the stent-graft. A sacrificial ePTFE crush tube about 0.25 mm thickness with a density of about 0.75 g/cc and fibril length of about 30 microns was placed over the skived tape layer and crushed into the interstices of the stent using a Blockwise Model G iris style crusher (Blockwise Engineering, Tempe Ariz.), thus compacting the stent-graft into contact with the underlying ePTFE sacrificial cushion tube. A sacrificial FEP shrink tube (Zeus Industrial Products, Inc., Orangeburg S.C.), with an expanded diameter of about 7 mm, retracted diameter of about 4 mm and a wall thickness of about 0.5 mm, was placed over the sacrificial ePTFE crush tube. Finally, a sacrificial 7.5 mm ID ePTFE outer cushion tube was fitted over the entire assembly and over the full length of the inner ePTFE cushion tube, this cushion tube being the same as previously described cushion tubes except for the ID.

The tapered portion of the 6 mm mandrel was inserted into a hot box chamber about 5.1 cm long, 2.5 cm in diameter, with openings in the entrance to provide some clearance for the outside diameter of the outer cushion tube before retraction (about 7.6 mm diameter) and at the exit to accommodate the outside diameter of the outer cushion tube over the shrink tube after retraction (about 6.4 mm diameter).

Figure 12:
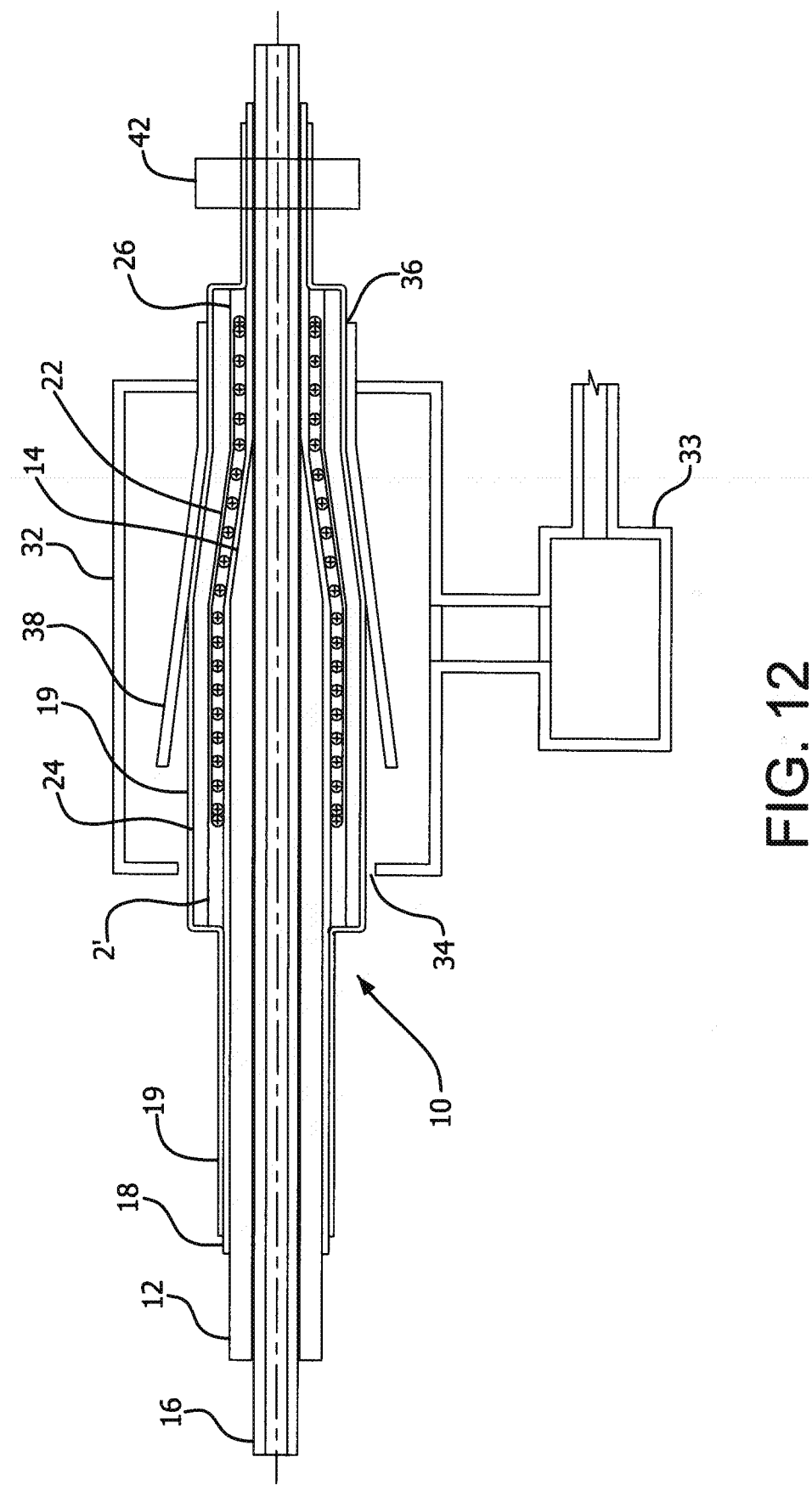
FIG. 12 is a longitudinal cross sectional view of the hot box chamber used for manufacturing of a diametrically extensible stent-graft.

FIG. 12 is a longitudinal cross section of the hot box chamber 32 showing the mandrel and graft assembly 10 as inserted into the hot box chamber 32 in the process of pulling the graft assembly 10 down from the 6 mm mandrel 12, and across the taper 14 of the 6 mm mandrel 12 (and between taper 12 and funnel 38 within hot box chamber 32; funnel 38 is unique to this example) onto the 4 mm mandrel 16. Funnel 38 is required to have the same 4° taper as the taper at the end of the 6 mm mandrel; the spacing between the taper 14 of the 6 mm mandrel and the funnel 38 should be appropriate to accommodate the thickness of the graft assembly 10. The hot box chamber 32 was attached to a heat source 33 (Balloon Development Station Model 210-A, Beahm Designs, Los Gatos Calif.) set to 240° C.

The graft assembly 10 was pulled through the entrance 34 to the hot box chamber 32, the chamber funnel 38, and chamber exit 36 by gripping clamp 42 and pulling the exposed end of the inner 18 and outer 19 cushion tubes onto the 4 mm mandrel 16. The graft assembly 10 was thus moved from the 6 mm mandrel 12, across the mandrel taper 14 (and through funnel 38), onto the 4 mm mandrel 16. As the shrink tube 24 entered the chamber 32 it shrank down onto the outside of the crush tube 26, thus holding the graft tightly against the mandrels 16, 12 and taper 14, causing the stent-graft 22 ID to be reduced to 4 mm without visibly wrinkling the luminal surface of the stent-graft 22. The fibrils in the FEP-coated ePTFE film wrapping of the stent-graft 22 were bent circumferentially and mingled with the FEP. The process was continued until the full length of the stent-graft 22 was pulled down onto the 4 mm mandrel 16, with the assembly 10 being fully removed from hot box 32.

The outer cushion tube 19 was removed and the remaining assembly 10 was removed from the 4 mm mandrel 16. The inner cushion tube 18 was then removed. The remaining assembly 10 was placed onto another 4 mm mandrel (not shown). The assembly was placed in a Blockwise Model G iris style crusher (Blockwise Engineering, Tempe Ariz.); crusher set points were 100° C. and 120 psi. Electrodes attached to a Magna-Power Electronics DC power supply, model XR10-200 (Magnapower Electronics, Flemington, N.J.), were attached to the mandrel. One hundred amps at about 2 volts was conducted through the mandrel and the graft assembly, causing the FEP coating on the ePTFE film to melt and flow into and at least partially through the bent fibrils of the film. Following the conclusion of the heating process, the crush pressure was released and the assembly was removed from the crusher. The shrink tube and crush tube were removed from the stent-graft, which was then removed from the mandrel.

The completed, diametrically compacted device can be returned to its original 6 mm diameter, or any diameter in-between, by the application of an inflating catheter balloon force to the luminal surface. Typically about 8-9 ATM of force is required to return the device to its full diameter.

The device thus manufactured can be loaded onto a catheter delivery system through a fluted metal funnel as described in U.S. Pat. No. 6,702,845 to Cully et al., and inserted into a remotely removable covering as described in U.S. Pat. No. 6,224,627 to Armstrong et al. The device can then be delivered to a selected vessel location, deployed by releasing the device from the covering, and ballooned as appropriate to fit the vessel. The resulting device will be substantially wrinkle free across its usable range and can be custom fitted to the ID of the vessel by the clinician appropriately to fit the vessel's anatomy.

Example 3: Length Adjustable Vascular Graft

A length adjustable 6 mm vascular graft was produced by making an about 25 cm long vascular graft in the method described above for the diametrically extensible graft. The graft was then placed on a 6 mm stainless steel mandrel, and then compressed longitudinally to a length of about 7.5 cm, or about 30% of its original length. In the process, the fibrils in the graft including the fibrils of the film become bent. The graft on the mandrel was placed in a 320° C. convection oven for 10 minutes. During this process the FEP on the film of the graft was melted and flows into the void spaces between the bent fibrils. After removal from the oven and cooling to about ambient temperature, the graft was removed from the mandrel. The length of the graft thus shortened was about 50% less than the original length. The FEP mingled with the bent fibrils retains the graft in its shortened length until it was manually extended by the application of a tensile force up to about its original precursor length. Some degree of foreshortening of the graft was observed, however the graft retained at least 90% of the length of the precursor tube after extension.

Examples 2 and 3 can be combined to make a graft that is length and diameter adjustable. The graft should be reduced in length first as described in Example 2, then can be made diameter adjustable using the process in Example 3.

Example 4: Diametrically Extensible Tube Having Bent Nodes

Figure 13:
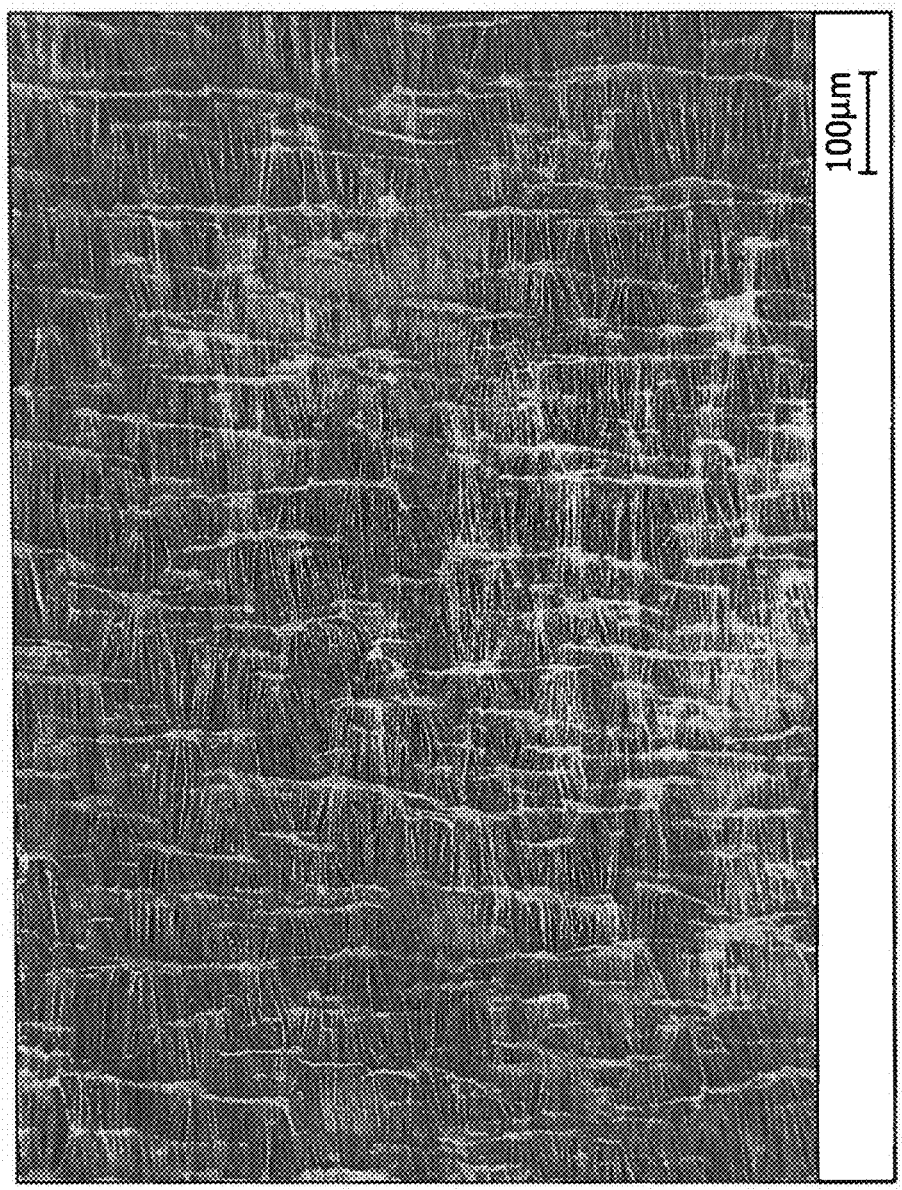
FIG. 13 is a scanning electron photomicrograph of an ePTFE film having a microstructure of nodes interconnected by fibrils.

A 4 mm ID tube with bent nodes to provide diametric adjustability out to 6 mm ID was produced using an ePTFE film with an area weight of about 5 g/m². The film, about 0.01 mm thickness, bulk density about 0.2 g/cc, having a microstructure of longitudinally oriented fibrils averaging about 80 micron average fibril length, and transversely oriented nodes averaging about 200 microns in length. A sample of this material is shown in FIG. 13. A sample of the film, 25 cm long and 8 cm wide, with the fibrils oriented longitudinally and nodes oriented circumferentially, was cigarette wrapped onto a 6 mm mandrel, yielding a tubular wrap 25 cm long with about 5 layers of the film. The tubular wrap was radially overwrapped with a sacrificial layer of Kapton slit to form a 2.5 cm wide tape to provide a compressive outer force. This tubular composite was then heated to 380° C. for 12 minutes to form a film tube. The Kapton wrap was removed and discarded. The resulting film tube was then removed from the mandrel.

A mandrel was procured having a 6 mm diameter for a portion of its length, and then tapering at an angle of 4° (the taper being measured off of the longitudinal axis of the mandrel), down to a 4 mm diameter for the remainder of the length of the mandrel. A 40 cm long 5 mm diameter sacrificial cushion tube as described previously, was fitted over the 6 mm diameter portion of the mandrel and extended 10 cm onto the 4 mm mandrel. The film tube was fitted over the cushion tube on the 6 mm portion of the mandrel about 3 cm back from the taper. A 12.7 mm wide strip of 1.5 mm thick sacrificial silicone strip 60 cm long was wrapped tightly around the sintered tube. The cushion tube was then grasped along the 4 mm portion of the mandrel and was used to pull the wrapped film tube down the taper onto the 4 mm mandrel. In the process, the film tube was contained by the taper on the inside and the tightly wrapped silicone strip on the outside. The result was that the circumferentially oriented nodes were bent microscopically while the film tube diameter was reduced from 6 to 4 mm, macroscopically wrinkle free.

Figure 14:
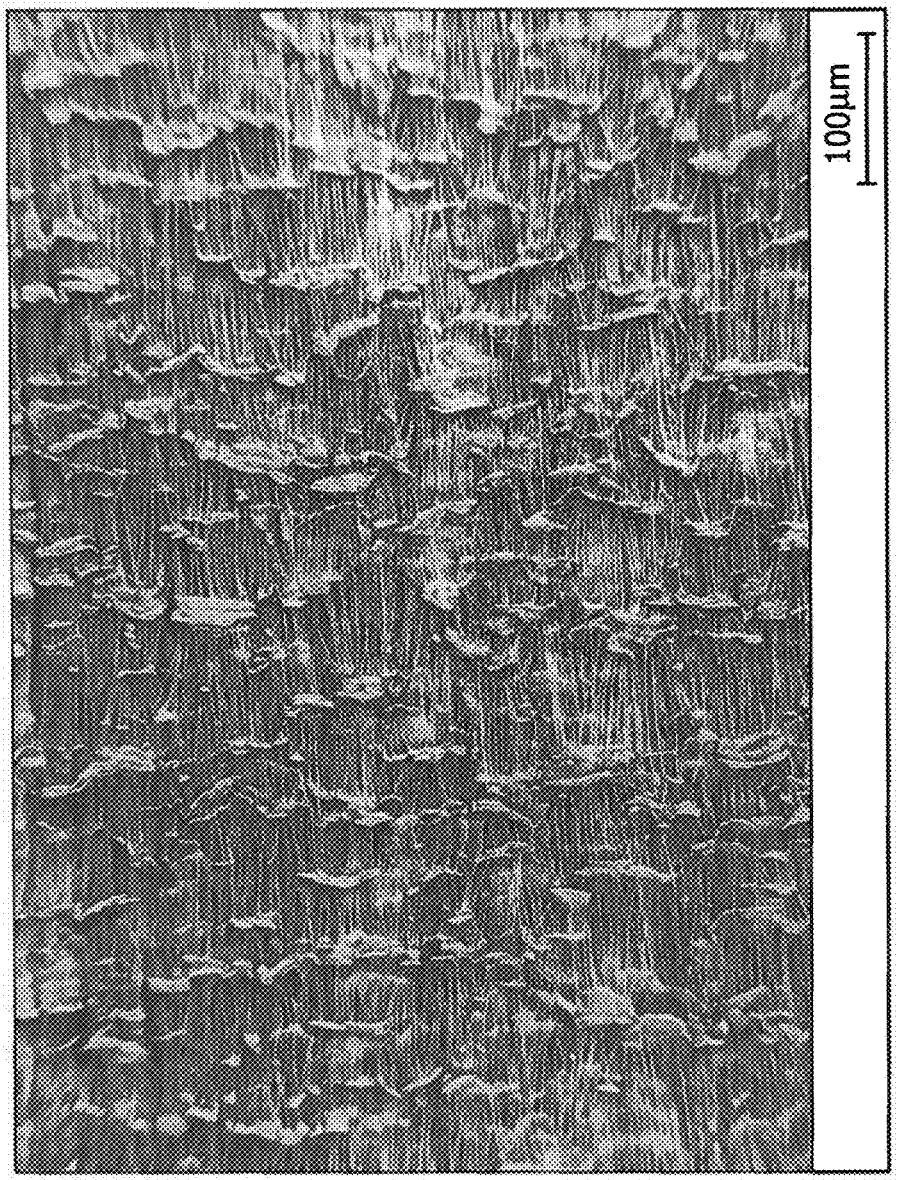
FIG. 14 is a scanning electron photomicrograph of an ePTFE film having a microstructure of nodes interconnected by fibrils (per FIG. 13), taken after the application of compression to the film in the direction of the length of the nodes, resulting in folding of the nodes (i.e., bent nodes).
Figure 15:
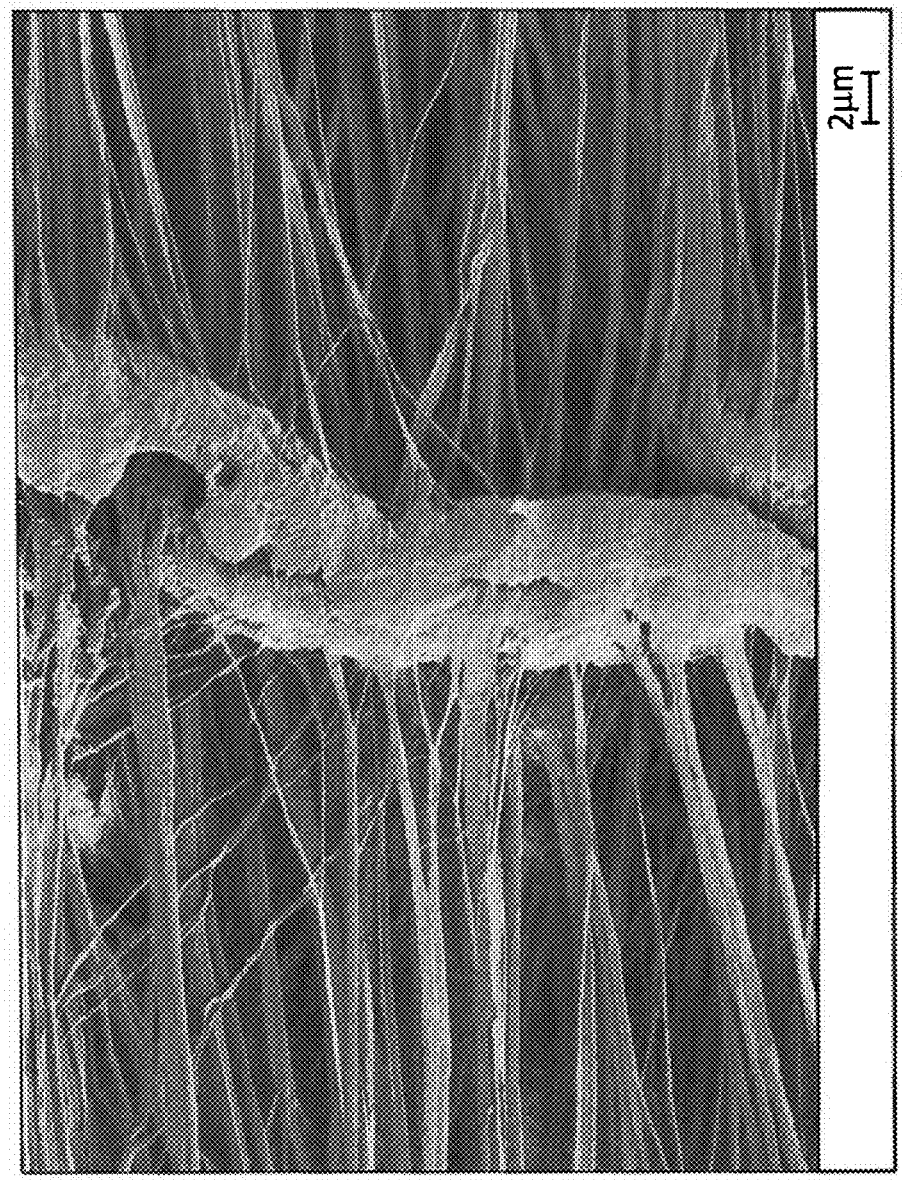
FIG. 15 is a scanning photomicrograph of a bent node that has been folded back on itself.

The assembly was placed in a 210° C. convection oven for 10 minutes to begin to set the bent form of the nodes. The silicone strip was then removed and a sacrificial layer of 0.012 mm skived PTFE (St. Gobain Performance Plastics, Paris, France) was tightly wrapped over the film tube. The film tube was placed in a 370° C. convection oven for 5 minutes, then removed and allowed to cool to ambient temperature. The skived PTFE tape was removed from the film tube, and then the film tube and cushion tube were removed from the mandrel and the cushion tube was removed from the ID of the film tube. The completed tube had bent nodes in the circumferential direction as shown in FIGS. 14 and 15.

Figure 16:
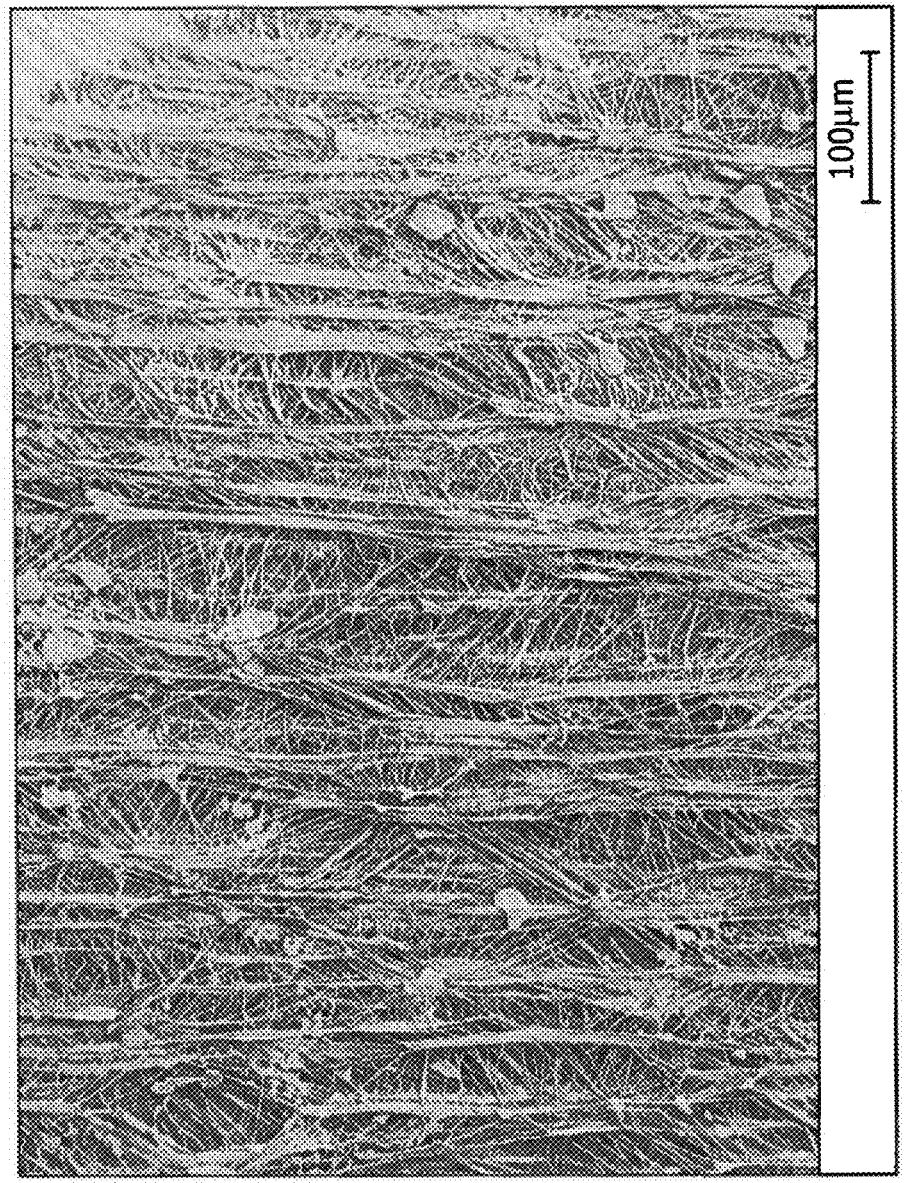
FIG. 16 is a scanning electron photomicrograph of an ePTFE film having a microstructure of nodes interconnected by fibrils, wherein the nodes have been folded per FIG. 14, following the application of a tensile force in the direction of the length of the nodes, sufficient to substantially straighten the nodes.

The film tube thus manufactured with bent nodes was placed on a 6 mm catheter balloon. The balloon was inflated and the film tube returned to its original 6 mm inside diameter. The nodes substantially returned to their original, unbent form as shown in FIG. 16.

For purposes of the present description, the average nodal length is determined by obtaining a photomicrograph of a surface of an ePTFE sample that shows a node and fibril microstructure at a magnification level that includes at least ten sequential nodes that intersect a line drawn across the length of the middle vertical region of the photomicrograph. The individual heights of ten sequential nodes taken beginning from left to right on the photomicrograph are determined by measuring with dividers referenced against a scale that accounts for the magnification factor. The ten heights are then averaged to provide the average nodal length.

Bent nodes will generally have an appearance of being substantially bent, i.e., bent in an amount of ninety degrees or more. These fibrils may be bent into 2 or 3 parallel segments (analogous to a letter U that has been flattened in a horizontal direction (e.g., similar to FIG. 15) or a letter Z that has been flattened in a vertical direction). More generally, bent nodes exist when, for a substantial portion of nodes within a given sample, at least 4 out of 10 nodes sampled from a photomicrograph as described above are determined to be bent in an amount of about 90 degrees of more.

Example 5: Self Expanding, Balloon Adjustable Stent-Graft with a Flared End

Figure 19:
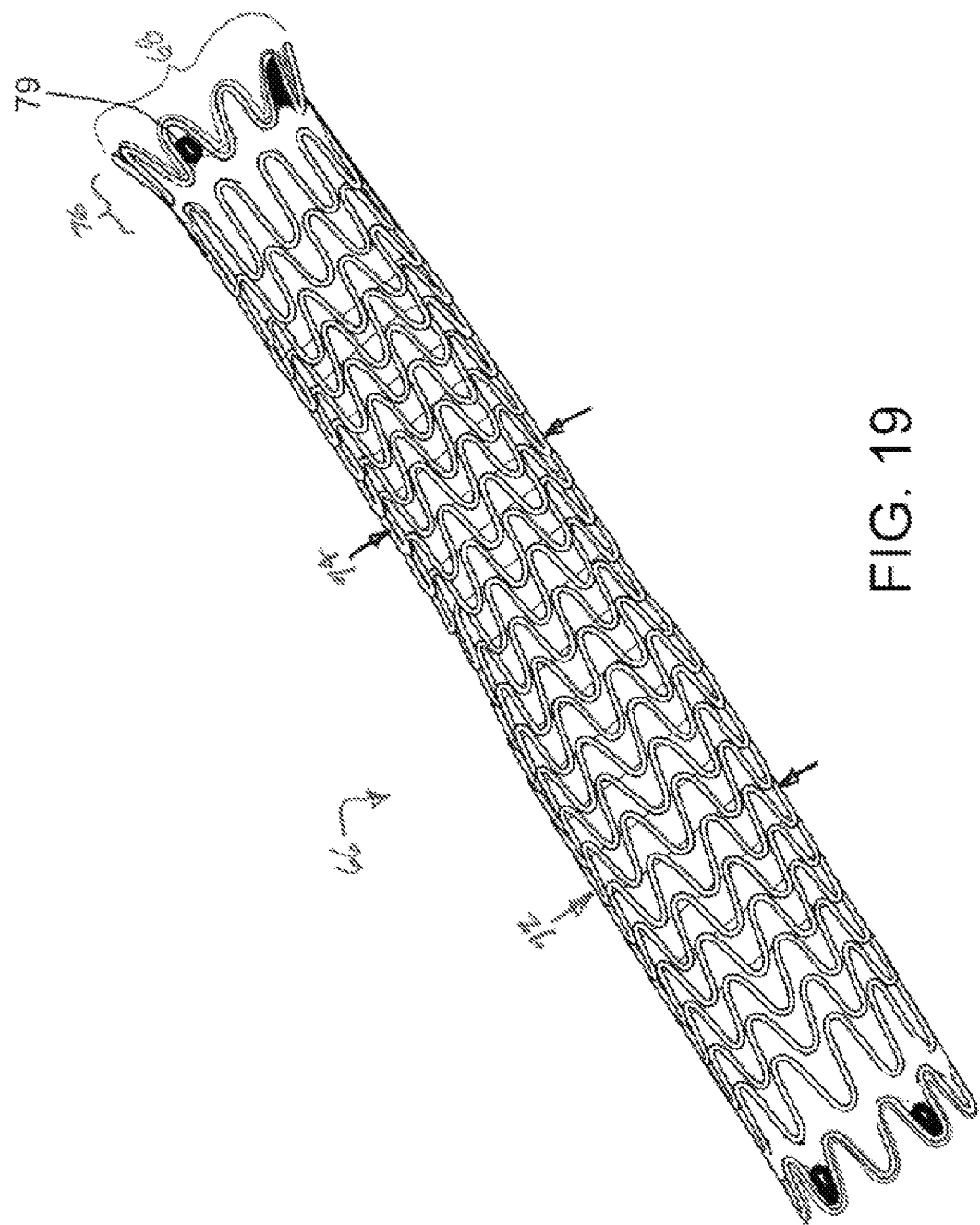
FIG. 19 is a self-expanding/balloon expandable stent-graft with an enlarged end.

Example 5 is the same as Example 2 with the exception of the helically wound serpentine wire stent portion. The helically wound stent as described in this example can have varying wire winding characteristics. One example of such a winding which can be used to make a self-expanding, balloon adjustable stent-graft 66 with a first portion, or flared end 76, and a second portion generally shown as the remainder of stent-graft 66 as shown in FIG. 19 is described herein. The stent-graft 66 self-expands from a constrained, compacted diameter (now shown in FIG. 19; the compacted diameter is suitable for passage through a vasculature to a desired deployment site) to an enlarged first diameter 74 and is balloon expandable to a larger second diameter 72. For illustrative purposes, only a portion of the length of the stent-graft has been mechanically expanded by a catheter balloon from the self-expanded first diameter 74 to the larger second diameter 72 in FIG. 19 (and FIG. 1). When the constraining sleeve is removed from the device at its compacted diameter and the stent-graft expands to its self-expanded state from its previous compacted state (i.e., compacted diameter), the flared end 76 self-expands to a maximum diameter 68 that is greater than the self-expanded, enlarged first diameter 74 and is approximately equal to the fully balloon expanded, larger maximum second diameter 72.

Figure 17:
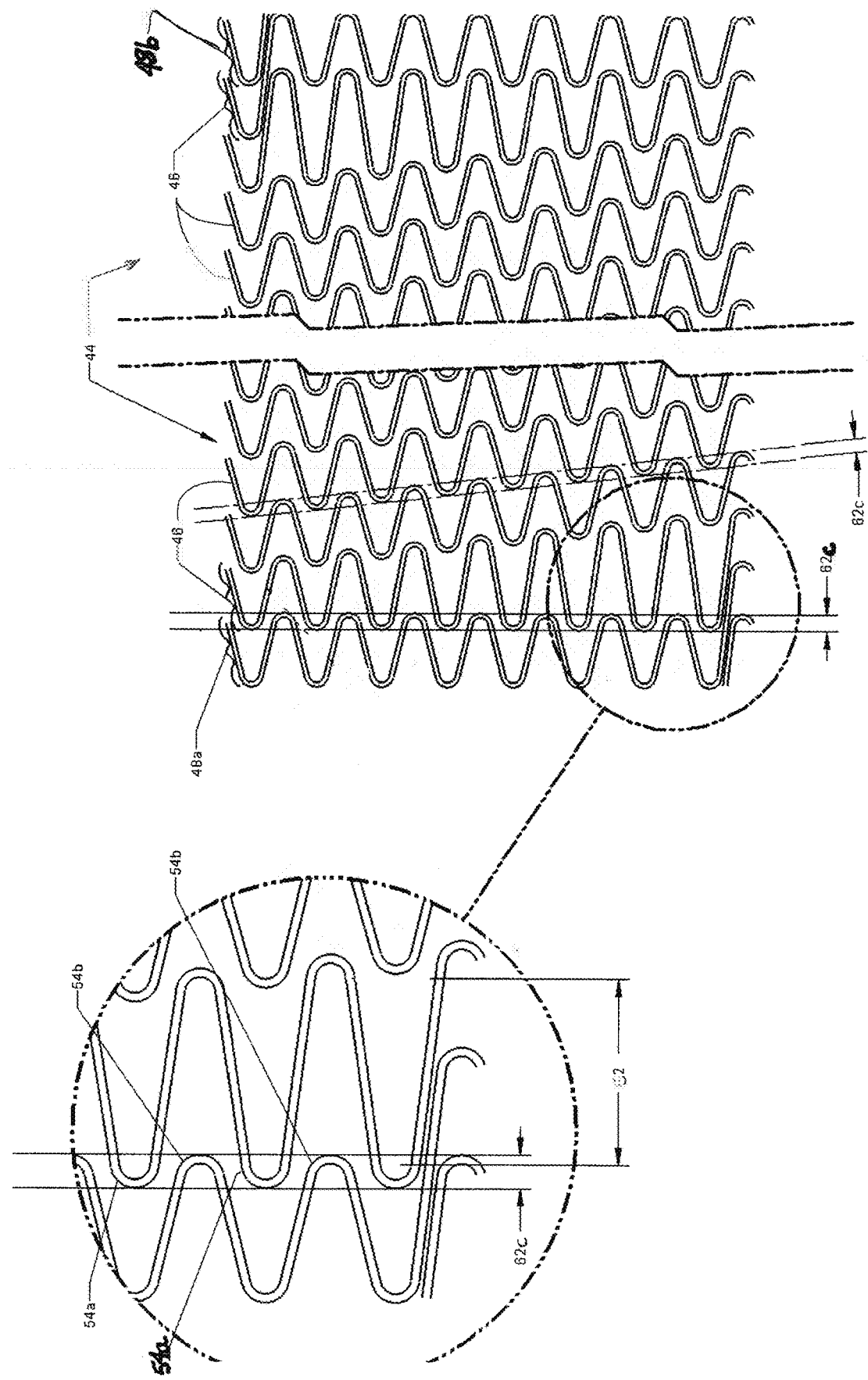
FIG. 17 is a flat pattern view of a helically wound stent-graft in accordance with the stent-graft shown in FIG. 1.
Figure 18:
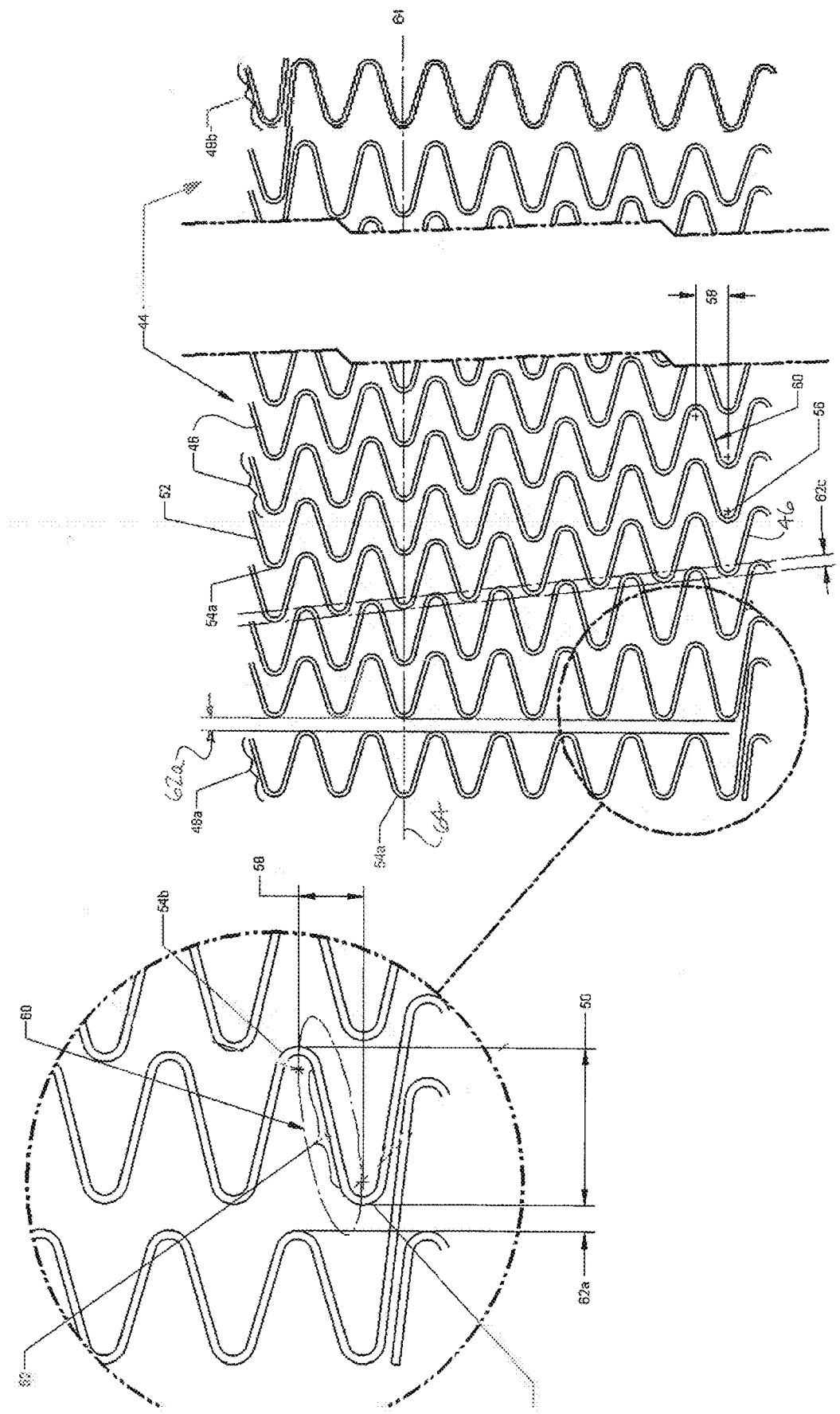
FIG. 18 is a flat pattern view of a helically wound stent-graft in accordance with the stent-graft shown in FIG. 19.

A self-expanding, balloon stent-graft 66 with a flared end 76 as shown in FIG. 19, has winding characteristics as shown in the flat pattern described by FIG. 18. This flat pattern 44 represents the appearance of the stent-graft 66 as it would appear if cut in a straight line along its length (i.e., cut along a line parallel to the longitudinal axis of the tubular form) and laid out flat. Flat pattern 44 of the helically wound stent or stent-graft 66 as shown in FIG. 18 has body row (or intermediate row) windings 46 located between end row windings 48a, corresponding with a first end of the stent-graft 66, also described as a first terminal end, and 48b, corresponding to a second end of the stent-graft 66, also described as a second terminal end, opposite the first end. In other embodiments, the end row windings 48a may correspond to the second end of the stent-graft 66, while the first end of the stent-graft 66 may correspond to the end row windings 48b. Each individual winding 60 within a row winding has a straight wire portion 52 extending between curved wire apices 54a and 54b. Dimension 50 (i.e. amplitude 50) of an individual winding 60 is measured as the distance or height between adjacent opposing apices 54a and 54b of the same winding. Dimension 58 is the circumferential distance between adjacent apices within an individual winding 60 and is measured from the center of the apices 54a and 54b as shown. The apices 54a and 54b of an individual winding 60 can overlap with an adjacent winding as shown by dimension 62c (FIGS. 17 and 18) or be spaced apart as shown by 62a (FIG. 18). Overlap is defined as when apices of one winding intrude into the space defined by the amplitude 50 of an adjacent winding as shown by dimension 62c which represents the amount of overlap.

FIG. 18 shows how an apex 54a of an end row winding 48a is substantially aligned to an apex 54a of an adjacent body row winding 46 and an apex 54a of the opposing end row winding 48b along phantom line 64 which runs along the length of the surface of the stent-graft and is parallel to a longitudinal axis of the tubular form of the stent-graft. FIG. 18 also shows how the body rows 46 have overlap with adjacent body rows and the end rows 48a and 48b have no overlap with adjacent body winding rows 46. This lack of overlap at the end rows augments the flaring of the flared end when the stent-graft is deployed from its compacted state to its self-expanded state. Additionally shown in FIG. 18 is how end winding rows 48a and 48b (as well as the winding rows immediately adjacent to end rows 48a and 48b) may be optionally provided with a serpentine form having a greater amplitude 50 (resulting from longer straight wire portions 52) than the amplitude 50 of body windings 46. Longer straight wire portions may be successively shortened with each successive straight wire portion to achieve, for example, body windings 46 with shorter straight wire portions 52.

FIG. 17 is the flat pattern view of the stent associated with the stent-graft embodiment of FIG. 1 where the apices 54b of the end row 48a overlap with the apices of an adjacent body row 46 shown by dimension 62c. It is also shown by dimension 62c how the apices of the body rows 46 overlap with adjacent body winding rows. It can be appreciated how overlap can occur within body rows or within a body row and an end row. When the end row 48a or 48b of a stent has overlap 62c with an adjacent row 46, the end row is more limited in its ability to form a flared end during self-expansion of the stent-graft from its compacted state to its fully self-expanded first diameter.

FIG. 19 shows a magnified image of a self-expanding, balloon adjustable stent-graft 66 with a flared end 76, generally having a stent geometry as shown in FIG. 18. The flared end 76 has a maximum diameter 68, after a constraining sleeve has been removed and the stent-graft has self-expanded to the first diameter 74. The stent-graft can then be ballooned up from the self-expanded state 74 (first diameter 74) to a larger ballooned state 72. Stent-graft 66 may optionally be provided with radiopaque markers 77 known to those of skill in the art.

In addition to being directed to the teachings described above and claimed below, devices and/or methods having different combinations of the features described above and claimed below are contemplated. As such, the description is also directed to other devices and/or methods having any other possible combination of the dependent features claimed below.

Numerous characteristics and advantages have been set forth in the preceding description, including various alternatives together with details of the structure and function of the devices and/or methods. The disclosure is intended as illustrative only and as such is not intended to be exhaustive. It will be evident to those skilled in the art that various modifications may be made, especially in matters of structure, materials, elements, components, shape, size and arrangement of parts including combinations within the principles of the invention, to the full extent indicated by the broad, general meaning of the terms in which the appended claims are expressed. To the extent that these various modifications do not depart from the spirit and scope of the appended claims, they are intended to be encompassed therein.

The invention claimed is:

1. A diametrically expandable medical device comprising:
   a stent-graft including,
   a stent defining a length, an inner stent surface, and an outer stent surface, and
   a graft covering on either or both of the inner and outer stent surfaces along at least a portion of the length of said stent-graft, the graft covering including a substrate comprising a fracturable material,
   the stent-graft terminating at a first terminal end and a second terminal end opposite the first terminal end, the stent-graft having a diametrically compacted diameter for insertion into a body conduit, the stent-graft including a first portion and a second portion;
   the first portion of the stent-graft extending from the first terminal end of the stent graft, the first portion defining a length, the first portion being self-expandable from the compacted diameter to an expanded state in which the first portion flares radially outward and increases in diameter along an entirety of the length of the first portion such that the first terminal end of the stent defines a maximum diameter of the first portion, and
   the second portion of the stent-graft being self-expandable from the compacted diameter to an enlarged, intermediate diameter at which the second portion of the stent-graft is maintained by the graft covering, the second portion of the stent-graft configured to remain at the intermediate diameter within the body conduit until a mechanical expansion force is imparted onto the second portion of the stent-graft, the mechanical expansion force facilitating further deployment of the stent-graft from the enlarged, intermediate diameter to a still larger, enlarged, maximum diameter by fracturing the fracturable material of the graft covering through the mechanical expansion force;
   wherein when the first portion of said stent-graft is in the expanded state, and the second portion is at the enlarged, maximum diameter, the maximum diameter of the first portion, which is located at the first terminal end of the stent-graft, is about the same as the enlarged, maximum diameter of the second portion of the stent-graft.

2. A diametrically expandable medical device according to claim 1 wherein the mechanical expansion is accomplished with a catheter balloon.

3. A diametrically expandable medical device according to claim 1 wherein the stent-graft comprises nitinol.

4. A diametrically expandable medical device according to claim 1 wherein the stent-graft comprises nitinol wire.

5. A diametrically expandable medical device according to claim 1 wherein the stent-graft comprises helically wound wire having a serpentine form with apices pointing alternately toward opposite ends of the device.

6. A diametrically expandable medical device according to claim 5 wherein adjacent windings of the helically wound wire are spaced further apart at ends of the device than are adjacent windings of the helically wound wire in a middle region of the device.

7. A diametrically expandable medical device according to claim 6 wherein said substrate provided with the fracturable material defines a fracturable film.

8. A diametrically expandable medical device according to claim 7 wherein the substrate comprises ePTFE.

9. A diametrically expandable medical device according to claim 8 wherein the fracturable material comprises fluorinated ethylene propylene.

10. A diametrically expandable medical device according to claim 7 wherein the fracturable material comprises fluorinated ethylene propylene.

11. A diametrically expandable medical device according to claim 1 wherein said substrate provided with the fracturable material defines a fracturable film.

12. A diametrically expandable medical device according to claim 11 wherein the substrate comprises ePTFE.

13. A diametrically expandable medical device according to claim 12 wherein the fracturable material comprises fluorinated ethylene propylene.

14. A diametrically expandable medical device according to claim 11 wherein the fracturable material comprises fluorinated ethylene propylene.

15. A diametrically expandable medical device according to claim 1 wherein said stent-graft is deployed to the enlarged, maximum second diameter, the maximum diameter of the first terminal end remains equal to about the enlarged, maximum second diameter of said stent-graft.

16. A diametrically expandable medical device that comprises:
a stent-graft having a length extending between a first terminal end and a second terminal end, and multiple rows of expandable elements, the stent-graft being expandable from a first, compacted configuration, to a second, intermediate configuration, and from the second, intermediate configuration to a third, fully expanded configuration, the stent graft including,
a stent defining an inner stent surface, and an outer stent surface, and
a graft covering on either or both of the inner and outer stent surfaces along at least a portion of the length of said stent-graft, the graft covering including a fracturable film; and
wherein the stent-graft has a first end portion terminating at a first terminal end of the stent-graft, a second end portion terminating at a second terminal end of the stent-graft, and a mid-portion between the first end portion and the second end portion,
wherein the stent-graft is self-expandable from the first, compacted configuration in which the first end portion, the second end portion, and the third end portion are in a diametrically compacted state to the second, intermediate configuration that includes at least the mid-portion of the stent graft being maintained by the graft covering at a first enlarged diameter,
wherein the stent-graft is configured to remain at the second, intermediate configuration until a mechanical expansion force is imparted onto the stent-graft to facilitate the stent-graft to be enlarged from the second, intermediate configuration to the third, fully expanded configuration in which the mid-portion of the stent-graft is enlarged to a larger, maximum second diameter upon application of the mechanical expansion force against the device sufficient to fracture the fracturable film of the graft covering via the mechanical expansion force;
wherein when the stent-graft is in the second, intermediate configuration with the mid-portion of the stent-graft at the enlarged first diameter the second end portion flares radially outward away from the mid-portion along an entire length thereof such that the second end portion achieves a maximum diameter at the second terminal end of the stent-graft, the maximum diameter of the second terminal end being about equal to the larger, maximum second diameter that the mid-portion of the stent-graft would exhibit at the third, fully expanded configuration, and
wherein the maximum diameter of the second terminal end of the stent-graft does not substantially change as the stent-graft is expanded from the second, intermediate configuration in which the mid-portion is at the first enlarged diameter to the third, fully expanded configuration in which the mid-portion is at the larger, maximum second diameter.

17. A diametrically expandable medical device according to claim 16 wherein the mechanical expansion is accomplished with a catheter balloon.

18. A diametrically expandable medical device according to claim 16 wherein the stent-graft comprises nitinol.

19. A diametrically expandable medical device according to claim 16 wherein the stent-graft comprises nitinol wire.

20. A diametrically expandable medical device according to claim 16 wherein the expandable elements comprise helically wound wire having a serpentine form with apices pointing alternately toward opposite ends of the device.

21. A diametrically expandable medical device according to claim 20 wherein adjacent windings of the helically wound wire are spaced further apart at ends of the device than are adjacent windings of the helically wound wire in a middle region of the device.

22. A diametrically expandable medical device according to claim 21 wherein the fracturable film comprises ePTFE.

23. A diametrically expandable medical device according to claim 22 wherein the fracturable film further comprises fluorinated ethylene propylene.

24. A diametrically expandable medical device according to claim 21 wherein the fracturable film comprises fluorinated ethylene propylene.

25. A diametrically expandable medical device according to claim 16 wherein the fracturable film comprises ePTFE.

26. A diametrically expandable medical device according to claim 25 wherein the fracturable film further comprises fluorinated ethylene propylene.

27. A diametrically expandable medical device according to claim 16 wherein the fracturable film comprises fluorinated ethylene propylene.

28. An implantable stent-graft having a proximal end and a distal end and an intermediate portion between the proximal and distal ends, the implantable stent-graft comprising:
a graft; and
a stent attached to the graft, the stent formed by a plurality of stent rows, each row having a plurality of apices, the plurality of stent rows including a plurality of body rows, a distal terminal end row on a first end of the stent, and a proximal terminal end row on an opposite end of the stent,
wherein the distal terminal end row flares radially outwardly to define a flared end of the stent-graft which flares radially outward such that the distal terminal end of the stent graft increases in diameter distally away from the intermediate portion, the stent-graft being self-expandable to a first enlarged diameter at which at least a portion of the stent-graft is maintained by the graft covering, the portion of stent-graft configured to remain at the first enlarged diameter until a mechanical expansion force is imparted on the stent-graft, the mechanical expansion force facilitating further enlargement of the stent a larger, maximum second diameter upon application of the mechanical expansion force against the device sufficient to fracture a fracturable film of the graft covering via the mechanical expansion force, wherein the flared end of the stent-graft does not substantially increase in diameter as the device is expanded to the larger, maximum second diameter from the first enlarged diameter.

29. A diametrically expandable device comprising:
a support and a cover, the cover including a substrate provided with a fracturable material;
the support terminating at a first terminal end and a second terminal end opposite the first terminal end, the support having a diametrically compacted diameter for insertion into a conduit, the support including a first portion and a second portion;
the first portion of the support extending from the first terminal end of the support, the first portion defining a length, the first portion being self-expandable from the compacted diameter to an expanded state in which the first portion flares radially outwardly and increases in diameter along an entirety of the length of the first portion such that the first terminal end of the support defines a maximum diameter of the first portion, and
the second portion of the support being self-expandable from the compacted diameter to an enlarged, intermediate diameter at which the second portion of the support is maintained by the cover, the second portion of the support configured to remain at the intermediate diameter until a mechanical expansion force is imparted onto the second portion of the support, the mechanical expansion force facilitating further deployment of the support from the enlarged, intermediate diameter to a still larger, enlarged, maximum diameter by fracturing the fracturable material of the cover via the mechanical expansion force;
wherein when the first portion of said support is in the expanded state, and the second portion is at the enlarged, maximum diameter, the maximum diameter of the first portion, which is located at the first terminal end of the support, is about the same as the enlarged, maximum diameter of the second portion of the support.

30. A diametrically expandable medical device that comprises:
a support having a length extending between a first terminal end and a second terminal end, the support being expandable from a first, compacted configuration, to a second, intermediate configuration, and from the second, intermediate configuration to a third, fully expanded configuration, the support including a cover including a fracturable film;
wherein the support has a first end portion terminating at a first terminal end of the support, a second end portion terminating at a second terminal end of the stent-graft, and a mid-portion between the first end portion and the second end portion;
wherein the support is self-expandable from the first, compacted configuration in which the first end portion, the second end portion, and the third end portion are in a diametrically compacted state to the second, intermediate configuration that includes at least the mid-portion of the support being maintained by the cover at a first enlarged diameter,
wherein the support is configured to remain at the second, intermediate configuration until a mechanical expansion force is imparted onto the support, the mechanical expansion force facilitating the enlargement of the support from the second, intermediate configuration to the third, fully expanded configuration in which the mid-portion of the support is enlarged to a larger, maximum second diameter upon application of the mechanical expansion force against the device sufficient to fracture the fracturable film of the graft covering via the mechanical expansion force;
wherein when the support is in the second, intermediate configuration with the mid-portion of the support at the enlarged first diameter the second end portion flares radially outward away from the mid-portion along an entire length thereof such that the second end portion achieve a maximum diameter at the second terminal end of the support, the maximum diameter of the second terminal end being about equal to the larger, maximum second diameter that the mid-portion of the support would exhibit at the third, fully expanded configuration, and
wherein the maximum diameter of the second terminal end of the support does not substantially change as the support is expanded from the second, intermediate configuration in which the mid-portion is at the first enlarged diameter to the third, fully expanded configuration in which the mid-portion is at the larger, maximum second diameter.

* * * * *